(12) United States Patent
Palsson et al.

(10) Patent No.: US 6,667,034 B2
(45) Date of Patent: *Dec. 23, 2003

(54) METHODS FOR REGULATING THE SPECIFIC LINEAGES OF CELLS PRODUCED IN A HUMAN HEMATOPOIETIC CELL CULTURE, METHODS FOR ASSAYING THE EFFECT OF SUBSTANCES ON LINEAGE-SPECIFIC CELL PRODUCTION, AND CELL COMPOSITIONS PRODUCED BY THESE CULTURES

(75) Inventors: Bernhard O. Palsson, La Jolla, CA (US); R. Douglas Armstrong, Ann Arbor, MI (US); Michael F. Clarke, Ann Arbor, MI (US); Stephen G. Emerson, Ann Arbor, MI (US)

(73) Assignee: The Regents of the University of Michigan, Ann Arbor, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/857,594

(22) Filed: May 16, 1997

(65) Prior Publication Data

US 2003/0087432 A1 May 8, 2003

Related U.S. Application Data

(63) Continuation of application No. 08/334,011, filed on Nov. 2, 1994, now Pat. No. 5,635,386, which is a continuation of application No. 07/815,513, filed on Jan. 2, 1992, now abandoned, which is a continuation-in-part of application No. 07/740,590, filed on Aug. 5, 1991, now Pat. No. 5,399,493, which is a continuation-in-part of application No. 07/737,024, filed on Jul. 29, 1991, now abandoned, which is a continuation-in-part of application No. 07/628,343, filed on Dec. 17, 1990, now abandoned, which is a continuation-in-part of application No. 07/366,639, filed on Jun. 15, 1989, now abandoned.

(51) Int. Cl.[7] .................. A01N 63/00; A01N 65/00; C12N 5/00; C12N 5/02
(52) U.S. Cl. ............... 424/93.7; 424/93.1; 435/377; 435/383; 435/384; 435/385; 435/386
(58) Field of Search ................. 424/93.21; 435/283.1, 435/383, 377

(56) References Cited

U.S. PATENT DOCUMENTS

| | | | |
|---|---|---|---|
| 4,135,975 A | 1/1979 | Lichtman et al. | 435/391 |
| 4,481,946 A | 11/1984 | Altshuler et al. | 604/6.12 |
| 4,486,188 A | 12/1984 | Altshuler et al. | 604/6.12 |
| 4,514,499 A | 4/1985 | Noll | 435/364 |
| 4,714,680 A | 12/1987 | Civin | 435/347 |
| 4,808,611 A | 2/1989 | Cosman | 514/12 |
| 4,810,643 A | 3/1989 | Souza | 435/69.5 |
| 4,847,201 A | 7/1989 | Kaswasaki et al. | 435/69.5 |
| 4,861,714 A | 8/1989 | Dean et al. | 435/69.1 |
| 4,889,812 A | 12/1989 | Guinn et al. | 435/286.7 |
| 4,963,489 A | 10/1990 | Naughton et al. | 435/1.1 |
| 4,965,204 A | 10/1990 | Civin | 530/388.7 |
| 5,032,407 A | 7/1991 | Wagner et al. | 800/23 |
| 5,032,508 A | 7/1991 | Naughton et al. | 435/32 |
| 5,061,620 A | 10/1991 | Tsukamoto et al. | 435/7.21 |
| 5,199,942 A | 4/1993 | Gillis | 604/4.01 |
| 5,399,493 A | 3/1995 | Emerson et al. | 435/456 |
| 5,605,822 A | 2/1997 | Emerson et al. | 435/373 |
| 5,635,386 A | 6/1997 | Palsson et al. | 435/372 |
| 5,646,043 A | 7/1997 | Emerson et al. | 435/373 |
| 5,670,147 A | 9/1997 | Emerson et al. | 424/93.1 |
| 5,670,351 A | 9/1997 | Emerson et al. | 435/440 |
| 5,811,094 A | 9/1998 | Caplan et al. | 424/93.7 |
| 5,851,832 A * | 12/1998 | Weiss et al. | 435/368 |
| 5,922,597 A | 7/1999 | Verfaillie et al. | 435/372.1 |
| 5,945,225 A | 8/1999 | Speith-Herfurth et al. | 428/516 |
| 6,299,650 B1 | 10/2001 | Van Blitterswijk et al. | 623/23.63 |
| 6,326,198 B1 * | 12/2001 | Emerson et al. | 435/373 |

FOREIGN PATENT DOCUMENTS

| | | |
|---|---|---|
| EP | 0 358 506 | 3/1990 |
| EP | 0 455 482 | 11/1991 |
| WO | 90/15877 A2 | 12/1990 |
| WO | 93/18136 | 9/1993 |
| WO | 93/18137 | 9/1993 |
| WO | 95/06409 | 3/1995 |

OTHER PUBLICATIONS

Dunbar et al. Gene transfer into hematopoietic progenitor and stem cells: Progress and problems. Stem Cells 12: 563–576. 1994.*

(List continued on next page.)

Primary Examiner—Anne-Marie Falk
(74) Attorney, Agent, or Firm—Oblon, Spivak, McClelland, Maier & Neustadt, P.C.

(57) ABSTRACT

Methods, including culture media conditions, which provide for in vitro human stem cell division and/or the optimization of human hematopoietic progenitor cell cultures and/or increasing the metabolism or GM-CSF secretion or IL-6 secretion of human stromal cells and/or a method for assaying the effect of a substance or condition on a human hematopoietic cell population, and/or depleting the malignant cell or T-cell and B-cell content of a human hematopoietic cell population are disclosed. The methods rely on culturing human stem cells and/or human hematopoietic progenitor cells and/or human stromal cells in a liquid culture medium which is replaced, preferably perfused, either continuously or periodically, at a rate of 1 ml of medium per ml of culture per about 24 to about 48 hour period, and removing metabolic products and replenishing depleted nutrients while maintaining the culture under physiologically acceptable conditions. Optionally, growth factors are added to the culture medium. The disclosed culture conditions afford improved methods for bone marrow transplantation.

7 Claims, No Drawings

OTHER PUBLICATIONS

Friedmann et al. Overcoming the obstacles to gene therapy. Sci. Am. pp. 96–101. Jun. 1997.*

Orkin and Motulsky. Report and recommendations of the panel to assess the NIH investment in research on gene therapy. Dec. 1995.*

Verma et al. Gene therapy—promises, problems and prospects. Nature 389: 239–242. Sep. 1997.*

Kuby, J. (1994) Clinical Transplantation in Immunology, 2$^{nd}$ edition, p. 573.*

M. W. Glacken et al., "Mammalian cell culture: engineering principles and scale-up", Trends in Biotechnology, vol. 1, No. 4, 1983, pp. 102–108.

Steven A. Rosenberg et al., "in Vitro Growth of Murine T Cells II. Growth of In Vitro Sensitized Cells Cytotoxic for Alloantigens", The Journal of Immunology, vol. 121, No. 5. Nov. 1978, pp. 1951–1955.

W. French Anderson, "Prospects for Human Gene Therapy", Science, vol. 26, Oct. 26, 1987, pp. 401–409.

T.M. Dexter, "The Message in the medium", Nature, vol. 309, Jun. 1984, pp. 746–747.

Manfred R. Koller, et al. "Expansion of Primitve Human Hematopoietic Progenitors in a Perfusion Bioreactor System with LL–3, LL–6, and Stem Cell Factor", Biotechnology, vol. 11, Mar., 1993, pp. 358–363.

Bernhard O. Palsson et al., "Expansion of Human Bone Marrow Progenitor Cells in a High Cell Density Continuous Perfusion System", Biotechnology, vol. 11, Mar., 1993, pp 368–372.

Giovanni MiGliaccio et al., "In Vitro Differentiation of Human Granulocyte/Macrophage and Erythroid Progenitors: Comparative Analysis of the Influence of Recombinant Human Erythropoietin, G–CSF, GM–CSF, and IL–3 in Serum–Supplemented and Serum–Deprived Cultures", Blood, vol. 72, No. 1 Jul. 1988, pp. 248–255.

Ian K. McNiece et al., "Studies on the Myeloid Synergistic Factor from 5637: Comparison with Interleukin–1 Alpha", Bloo vol. 73, No. 4 (Mar.), 1989, pp. 919–923.

Paul Baines et al., Exp. Hematol. 16:785–789 (1988).

Jan A. Nolta et al., Human Gene Therapy, 1:257–268 (1990).

John R. Stephenson et al., Proc. Nat. Acad. Sci. U.S.A., vol. 68, No. 7, pp. 1542–1546, Jul. 1971.

Giovanni Migliaccio et al., Exp. Hematol. 18:1049–1055 (1990).

Richard M. Schwartz et al., "In Vitro Myelopoiesis Stimulated by Rapid Medium Exchange and Supplementation with Hematopoietic Growth Factors", Blood, vol. 78, No. 12, Dec. 15, 1991, pp. 3155–3161.

Rob E. Ploemacher et al., "Use of Limiting–Dilution Type Long–Term Marrow Cultures in Frequency Analysis of Marrow–Repopulating and Spleen Colony–Forming Hematopoietic Stem Cells in the Mouse", Blood, vol. 78, No. 10 Nov. 15, 1991, pp. 2527–2533.

Manfred R. Koller et al., "Effects of Synergistic Cytokine Combinations, Low Oxygen, and Irradiated Stroma on the Expansion of Human Cord Blood Progenitors", Blood, vol. 80, No. 2 (Jul. 15, 1992), pp. 403–411.

J. Aiken et al., Journal of Pediatric Surgery, vol. 25, No. 1 (Jan.), 1990; pp. 140–145.

C. Favre et al., "Interleukin–4 has Basophilic and Eosinophilic Cell Growth–Promoting Activity on Cord Blood Cells", Blood, vol. 1, Jan. 1, 1990, pp. 67–73.

Yoichi Takaue et al., "Limiting–Dilution Analysis of the Effects of Colony–Stimulated Factors, Phytohemagglutin, and Hydrocortisone on Hematopoietic Progenitor Cell Growth", Blood, vol. 70, No. 5, Nov., 1987, pp. 1611–1618.

Yoichi Takaue et al., "Effect of Recombinant Human G–CSF, GM–CSF, IL–3, and IL–1α on the Growth of Purified Human Peripheral Blood Progenitors", Blood, vol. 76, No. 2, Jul. 15, 1990, pp. 330–335.

H. J. Sutherland et al., "Alternative Mechanisms With and Without Steel Factor Support Primitive Human Hematopoiesis", Blood, vol. 81, No. 6., Mar. 15, 1993, pp. 1465–1470.

Lucia H. Coutinho et al., "Effects of Recombinant Human Granulocyte Colony–Stimulating Factor (CSF), Human Granulocyte Macrophage–CSF, and Gibbon Interleukin–3 on Hematopoiesis in Human Long–Term Bone Marrow Culture", Blood, vol. 11, Jun. 1, 1990, pp. 2118–2129.

Susan C. Guba et al., "Bone Marrow Stromal Fibroblasts Secrete Interleukin–6 and Granulocyte–Macrophage Colony–Stimulating Factor in the Absence of Inflammatory Stimulation: Demonstration by Serum–Free Bioassay, Enzyme–Linked Immunosorbent Assay, and Reverse Transcriptase Polymerase Chain Reaction", Blood, vol. 80, No. 5, Sep. 1, 1992, pp. 1190–1198.

Richard M. Schwartz et al., "Rapid medium perfusion rate significantly increases the productivity and longevity of human bone marrow cultures", Proc. Natl. Acad. Sci. USA, vol. 88, pp. 6760–6764, Aug. 1991.

David E. Harrison et al., "Primitive hemopoietic stem cells: direct assay of most productive populations by competitive repopulation with simple binomial, correlation and covariance calculations", Experimental Hematology 21:206–219 (1993).

D. Krumwieh et al., "Preclinical Studies on Synergistic Effects of IL–1, IL–3, G–CSF and GM–CSF in Cynomolgus Monkeys", International Journal of Cell Cloning 8:229–248, Suppl. 1 (1990).

Makio Ogawa, Ph.D., "Effects of Hemopoietic Growth Factors on Stem Cells in Vitro", Hematology/Oncology Clinics of North America, vol. 3(3) Sep. 1989, pp. 453–464.

Jerry Caldwell et al., "Culture Perfusion Schedules Influence the Metabolic Activity and Granulocyte–Macrophage Colony–Stimulating Factor Production Rates of Human Bone Marrow Stromal Cells"., Journal of Cellular Physiology, 147:344–353 (1991).

C.M. Heyworth et al., "The Role of Hemopoietic Growth Factors in Self–Renewal and Differentiation of IL–3–Dependent Multipotential Stem Cells"., Growth Factors, 1990, vol. 2, pp. 197–211.

Shiang Huang et al., "Formation of haematopoietic Microenvironment and haematopoietic stem cells from single human bone marrow stem cells", Nature, vol. 360, Dec. 24/31, 1992, pp. 745–749.

Randy A. Hock et al., "Retrovirus–mediated transfer and expression of drug resistance genes in human haematopoietic progenitor cells", Nature, vol. 320, Mar. 1986, pp. 275–277.

A.A. Fauser et al., "Granuloerythropoietic Colonies in Human Bone Marrow, Peripheral Blood, and Cord Blood" Blood, vol. 52, No. 6, Dec. 1978, pp. 1243–1248.

C.D. Myers et al., "A Cell Line Secreting Stimulating Factors for CFU–GEMM Culture", Blood, vol. 64, No. 1 (Jul.) 1984, pp. 152–155.

Alice M. Wang et al., "Molecular Cloning of the Complementary DNA for Human Tumor Necrosis Factor", Science, vol. 228, Nov. 20, 1984, pp. 149–154.

Colin A. Sieff et al., "Human Recombinant Granulocyte–Macrophage Colony–Stimulating Factor: A Multilineage Hematopoietin" Science, vol. 230, Dec. 6, 1985, pp. 1171–1173.

Robert E. Donahute et al., "Human IL–3 and GM–CSF Act Synergistically in Stimulating Hematopoiesis in Primates", Science, vol. 241, Sep. 30, 1988, pp. 1820–1823.

Ronald H. Schwartz, "A Cell Culture Model for T Lymphocyte Clonal Anergy", Science, vol. 248, Jun. 15, 1990, pp. 1349–1356.

Toshio Suda et al., "A Stimulatory Effect of Recombinant Murine Interleukine–7 (IL–7) on B–Cell Colony Formation and an Inhibitory Effect of IL–1$\alpha$", Blood, vol. 74, No. 6, Nov. 1, 1989, pp. 1936–1941.

Heather J. Sutherland et al., "Characterization and Partial Purification of Human Marrow Cells Capable of Initiating Long–Term Hematopoiesis In Vitro", Blood, vol. 74, No. 5 (Oct.), 1989; pp. 1563–1570.

Sem Seeland et al., "Combined and Sequential Effects of Human IL–3 and GM–CSF on the Proliferation of CD34+ Hematopoietic Cells from Cord Blood"., Blood, vol. 73, No. 5, (Apr.), 1989: pp. 1195–1201.

Sallie S. Boggs, "Targeted Gene Modification for Gene Therapy of Stem Cells", International Journal of Cell Cloning 8:80–96 (1990).

Angelika Mueller, "Die Knochenmarkstammzellkultur Technische Voraussetzungen und klinische Einsatzmoeglichkeiten", Folia Haematol., Leipzig 116 (1989) 5, 731–743.

Stephen G. Emerson et al., "Purification of Fetal Hematopoietic Progenitors and Demonstration of Recombinant Multipotential Colony–stimulating Activity", The Journal of Clinical Investigation, vol. 76, Sep. 1985, 1286–1290.

pp. 573–578: "Clinical Transplantation", In *Immunology*, Second Edition, J. Kuby, W.H. Freeman and Company, New York (1994).

Joseph Feder et al., "The Large–Scale Cultivation of Mammalian Cells", Scientific American, vol. 248, No. 1 (Jan. 1983), pp. 24–31.

Heather J. Sutherland, "Functional characterization of individual human hematopoietic stem cells cultured at limiting dilution on supportive marrow stromal layers", Proc. Natl. Acad. Sci. USA, vol. 87 (1990), pp. 3584–3588.

Janice L. Gabrilove et al., "Pluripoietin $\alpha$: A second human hematopoietic colony–stimulating factor produced by the human bladder carcinoma cell line 5637", Proc. Natl. Acad. Sci. USA, vol. 83, pp. 2478–2482, Apr. 1986.

Jeffrey A. Hubbell et al., Endothelial Cell–Selective Materials for Tissue Engineering in the Vascular Graft Via a New Receptor, Biotechnology, vol. 9, Jun. 1991, pp. 568–572.

Jerry Caldwell et al., "Influence of Medium Exchange Schedules on Metabolic, Growth, and GM–CSF Secretion Rates of Genetically Engineered NIHo–3T3 Cells", Biotechnology Progress, vol. 7, No. 1, Jan./Feb. 1991, pp. 1–8.

Li Lu et al., "Effect of recombinant and purified human haematopoietic growth factors on in vitro colony formation by enriched populations of human megakaryocyte progenitor cells", British Journal of Haematology, 1988, vol. 70, pp. 149–156.

A. Montes Borinaga et al., "Interleukin–6 is a cofactor for the growth of myeloid cells from human bone marrow aspirates but does not affect the clonogenicity of myeloma cells in vitro", British Journal of Haematology, 1990, No. 76, pp. 476–483.

P.M. Lehn., "Gene therapy using bone marrow transplantation: a 1990 update", Bone Marrow Transplantation (1990), No. 5, pp. 287–293.

Manfred R. Koller et al., "Beneficial Effects of Reduced Oxygen Tension and Perfusion in Long–Term Hematopoietic Cultures", Biochemical Engineering, VII, vol. 665 of the Annals New York Academy of Sciences, pp. 105–116, (Oct. 1992).

D. Krumwieh et al., "Human Recombinant Derived IL–3 and GM–CSF in Hematopoiesis of Normal Cynomolgus Monkeys", Behring Inst., Mitt., No. 83, pp. 250–257 (1988).

John Brandt et al., "Detection of Human Hematopoietic Progenitor Cell Capable of Forming Blast Cell Containing Colonies In Vitro", Advances in Experimental Medicine and Biology, vol. 241, pp. 165–173, (1988).

C.J. Eaves et al., "The Human Hematopoietic Stem Cell In Vitro and In Vivo", Blood Cells (1992) 18:301–307.

Masaaki Ishizuka et al., "Mitogenic Effect of Bestatin on Lymphocytes", The Journal of Antibiotics, vol. 33, No. 6, (Jun. 1980), pp. 653–662.

Donald B. Kohn Ph.D. et al., "Gene Therapy for Genetic Diseases", Cancer Investigation, 7(2), pp. 179–192 (1989).

Maria Podolak–Dawidziak et al., "Does Human Bladder Carcinoma Cell Line 5637–Conditioned Medium Supplement the Growth of Megakaryocyte Colonies (CFU–Mk) in Cultures of Human bone Marrow", Haematologia, 23:121–123 (1990).

Jan A. Nolta et al., "Comparison of the Effects of Growth Factors on Retroviral Vecto–Mediated Gene Transfer and the Proliferative Status of Human Hematopoietic Progenitor Cells", Human Gene Therapy, 1:257–268 (1990).

Christoph Heberlein et al., "The Gene for Erythropoietin Receptor is Expressed in Multipotential Hematopoietic and Embryonal Stem Cells: Evidence for Differentiation Stage–Specific Regulation", Molecular and Cellular Biology, vol. 12 (14) pp. 1815–1826, (1992).

Nicholas Dainlak et al., "Interactions of Insulin, Insulinlike Growth Factor II, and Platelet–derived Growth Factor in Erythropoietic Culture", J. Clin. Invest. vol. 76, Sep. 1985, 1237–1242.

Yves–Jacques Schneider et al., "Monoclonal Antibody Production in Semi–Continuous Serum–and protein–free culture", Journal of Immunological Methods, vol. 129 (1990) pp.251–268.

Philip W. Kantoff et al., "Expression of Human Adenosine Deaminase in Nonhuman Primates after Retrovirus–Mediated Gene Transfer", J. Exp. Med. vol. 166, Jul. 1987, pp. 219–234.

Suzanne Gartner et al., "Long–term culture of human bone marrow cells", Proc. Natl. Acad. Sci. USA, vol. 77, No. 8, pp. 4756–4759, Aug. 1980.

Kenneth C. Ehrlich et al., "Artificial Capillary Perfusion Cell Culture: Metabolic Studies", In Vitro, vol. 14, No. 5, 1978, pp. 443–450.

B. R. Jordan et al.,"Transformation of Murine LMTK–Cells with Purified HLA Class I Genes", Immunogenetics, 18:165–171, 1983.

E. Morioka et al, "Purification of a granulocyte colony–stimulating factor from the conditioned medium of a subclone of human bladder carcinoma cell line 5637, HTB9", Res. Exp. Med. (1990), 190:229–238.

Steven A. Rosenberg et al., "In Vitro Growth of Murine T Cells II. Growth of in Vitro Sensitized Cells Cytotoxic for Alloantigens", The Journal of Immunology, vol. 121, No. 5. Nov. 1978, pp. 1951–1955.

James Frank Parsons et al., "In Vitro Cell Perfusion. 1. System for Continuous Observation of Cells and Analysis of Perfusion Fluid Suitable for Isolated Mast Cell and Macrophage Studies", Journal of Pharmacological Methods vol. 8. pp. 073–089 (1982).

S. R. Adamson et al., "Industrial Mammalian Cell Culture", The Canadian Journal of Chemical Engineering, vol. 64, Aug. 1986, pp. 531–539.

Avshalom Mizrahi, "Production of Biologicals from Animal Cells an Overview", Process Biochemistry, (Aug. 1986), pp. 108–112.

Eastment and Rusceth, "Evaluation of Hematopoiesis in Long–Term Bone Marrow Culture: Comparison of Species Differences" In Long–Term Bone Marrow Culture, Kroc oundation Series vol. 18, Proceeding of a Symposium Held at the Kroc Foundation Santa Ynex Valley, California, Sep. 12–16, 1983.

Connie J. Eaves et al., "Methodology of Long–Term Culture of Human Hemopoietic Cells", J. Tiss. Cult. Meth 13:55–62, 1991.

R. Ian Freshney, "Culture of Animal Cells A Manual of Basic Technique", (1987) Department of Medical Oncology Cancer Research Campaign Laboratories University of Glasgow, Second Addition, pp. 305–307, Alan R. Liss, Inc. (New York).

Yu–Chung Yang et al., "Human IL–3 (Multi–CSF): Identification by Expression Cloning of a Novel Hematopoietic Growth Factor Related to Murine IL–3", Cell, vol. 47, pp. 3–10, Oct. 10, 1986.

* cited by examiner

METHODS FOR REGULATING THE SPECIFIC LINEAGES OF CELLS PRODUCED IN A HUMAN HEMATOPOIETIC CELL CULTURE, METHODS FOR ASSAYING THE EFFECT OF SUBSTANCES ON LINEAGE-SPECIFIC CELL PRODUCTION, AND CELL COMPOSITIONS PRODUCED BY THESE CULTURES

CROSS-REFERENCE TO RELATED APPLICATIONS

This application is a continuation of application Ser. No. 08/334,011, filed Nov. 2, 1994, now U.S. Pat. No. 5,635,386, which is a continuation of application Ser. No. 07/815,513, filed Jan. 2, 1992, abandoned, which is a continuation-in-part of application Ser. No. 07/740,590, filed Aug. 5, 1991, now U.S. Pat. No. 5,399,493, which is a continuation-in-part of application Ser. No. 07/737,024, filed Jul. 29, 1991, abandoned, which is a continuation-in-part of application Ser. No. 07/628,343, filed Dec. 17, 1990, abandoned, which is a continuation-in-part of application Ser. No. 07/366,639, filed Jun. 15, 1989, abandoned, which disclosures are incorporated herein by reference.

BACKGROUND OF THE INVENTION

1. Field of the Invention

The present invention relates to methods and compositions for the growth of mammalian cells in culture, particularly the growth of hematopoietic cell cultures. The present invention also relates to a functioning in vitro human tissue system, which may serve as a model for hematopoiesis. The present invention further relates to a method for assaying the effect of a substance and/or physical condition on a human hematopoietic cell mass or the hematopoietic process. The present invention also relates to a method for controlling the lineage development in an in vitro human tissue system and cultures of cells in which the population of a particular cell type has been enhanced relative to the total cell population in the culture or depleted. In addition, the present invention relates to a method of bone marrow tranplantation, in which the tissue implanted into the donee has been cultured by the present method.

2. Discussion of the Background

All of the circulating blood cells in the normal adult, including erythrocytes, leukocytes, platelets and lymphocytes, originate as precursor cells within the bone marrow. These cells, in turn, derive from very immature cells, called progenitors, which are assayed by their development into contiguous colonies of mature blood cells in 1–3 week cultures in semisolid media such as methylcellulose or agar.

Progenitor cells themselves derive from a class of progenitor cells called stem cells. Stem cells have the capacity, upon division, for both self-renewal and differentiation into progenitors. Thus, dividing stem cells generate both additional primitive stem cells and somewhat more differentiated progenitor cells. In addition to the generation of blood cells, stem cells also may give rise to osteoblasts and osteoclasts, and perhaps cells of other tissues as well. This document describes methods and compositions which permit, for the first time, the successful in vitro culture of human hematopoietic stem cells, which results in their proliferation and differentiation into progenitor cells and more mature blood cells of a specific lineage.

Although there are recent reports of the isolation and purification of progenitor cells (see, e.g., U.S. Pat. No. 5,061,620 as representative), such methods do not permit the long-term culture of viable and dividing stem cells.

In the late 1970s the liquid culture system was developed for growing hematopoietic bone marrow in vitro. The cultures are of great potential value both for the analysis of normal and leukemic hematopoiesis and for the experimental manipulation of bone marrow, for, e.g., retroviral-mediated gene transfer. These cultures have allowed a detailed analysis of murine hematopoiesis and have resulted in a detailed understanding of the murine system. In addition, it has made possible retroviral gene transfer into cultured mouse bone marrow cells. This allowed tagging murine hematopoietic cells proving the existence of the multi-potent stem cell and of the study of the various genes in the process of leukemogenesis.

But while it has been possible to transfer retroviral genes into cultured mouse bone marrow cells, this has not yet been possible in cultured human bone marrow cells because, to date, human long-term bone marrow cultures have been limited both in their longevity and more importantly in their ability to maintain stem cell survival and their ability to produce progenitor cells over time.

Human liquid bone marrow cultures were initially found to have a limited hematopoietic potential, producing decreasing numbers of progenitor cells and mature blood cells, with cell production ceasing by 6 to 8 weeks. Subsequent modifications of the original system resulted only in modest improvements. A solution to this problem is of incalculable value in that it would permit, e.g., expanding human stem cells and progenitor cells for bone marrow transplantation and for protection from chemotherapy, selecting and manipulating such cells, i.e., for gene transfer, and producing mature human blood cells for transfusion therapy.

Studies of hematopoiesis and in vitro liquid marrow cultures have identified fibroblasts and endothelial cells within adhering layers as central cellular stromal elements. These cells both provide sites of attachment for developing hematopoietic cells and can be induced to secrete hematopoietic growth factors which stimulate progenitor cell proliferation and differentiation. These hematopoietic growth factors include granulocyte colony stimulating factor (G-CSF), granulocyte-macrophage colony stimulating factor (GM-CSF) and interleukin 6 (IL-6).

Cultures of human bone marrow cells on such adherent layers in vitro however have been largely disappointing. Unlike related cultures from other species, such as mouse and tree shrew, human liquid marrow cultures fail to produce significant numbers of either nonadherent hematopoietic precursor cells or clonogenic progenitor cells for over 6 to 8 weeks. And although cultures lasting 3–5 months have been reported, no culture which stably produces progenitor cells from stem cells continuously for more than 4–6 weeks has been reported.

Moreover, nonadherent and progenitor cell production typically declined throughout even the short life of these cultures, so that it is not clear that stem cell survival or proliferation is supported at all by these cultures. Further, when studied in isolation, unstimulated bone marrow stromal cells secrete little if any detectable hematopoietic growth factors (HGFs).

The lack of stable progenitor cell and mature blood cell production in these cultures has led to the belief that they are unable to support continual stem cell renewal and expansion. It has therefore been presumed that the cultures either lack a critical stem cell stimulant(s) and/or contain a novel stem cell inhibitor(s). However, while explanations for failure to detect HGFs and uninduced stromal cell cultures have been suggested, the null hypothesis, which combines the failure to detect HGFs and the relative failure of human liquid marrow cultures, would be that the culture systems used in vitro do not provide the full range of hematopoietic supportive function of adherent bone marrow stromal cells in vivo.

Stem cell and progenitor cell expansion for bone marrow transplantation is a potential application of human long-term bone marrow cultures. Human autologous and allogeneic bone marrow transplantation are currently used as therapies for diseases such as leukemia, lymphoma and other life-threatening disorders. For these procedures however, a large amount of donor bone marrow must be removed to insure that there is enough cells for engraftment.

A culture providing stem cell and progenitor cell expansion would reduce the need for large bone marrow donation and would make possible obtaining a small marrow donation and then expanding the number of stem cells and progenitor cells in vitro before infusion into the recipient. Also, it is known that a small number of stem cells and progenitor cells circulate in the blood stream. If these stem cells and progenitor cells could be collected by phoresis and expanded, then it would be possible to obtain the required number of stem cells and progenitor cells for transplantation from peripheral blood and eliminate the need for bone marrow donation.

Bone marrow transplantation requires that approximately $1 \times 10^8$ to $2 \times 10^8$ bone marrow mononuclear cells per kilogram of patient weight be infused for engraftment. This requires the bone marrow donation of the same number of cells which is on the order of 70 ml of marrow for a 70 kg donor. While 70 ml is a small fraction of the donors marrow, it requires an intensive donation and significant loss of blood in the donation process. If stem cells and progenitor cells could be expanded ten-fold, the donation procedure would be greatly reduced and possibly involve only collection of stem cells and progenitor cells from peripheral blood and expansion of these stem cells and progenitor cells.

Progenitor cell expansion would also be useful as a supplemental treatment to chemotherapy and is another application for human long-term bone marrow cultures. The dilemma faced by the oncologist is that most chemotherapy agents used to destroy cancer act by killing all cells going through cell division. Bone marrow is one of the most prolific tissues in the body and is therefore often the organ that is initially damaged by chemotherapy drugs. The result is that blood cell production is rapidly destroyed during chemotherapy treatment and chemotherapy must be terminated to allow the hematopoietic system to replenish the blood cell supply before a patient is retreated with chemotherapy. It may take a month or more for the once quiescent stem cells to raise up the white blood cell count to acceptable levels to resume chemotherapy during which case the drop in blood cell count is repeated. Unfortunately, while blood cells are regenerating between chemotherapy treatments, the cancer has time to grow and possibly become more resistant to the chemotherapy drugs due to natural selection.

To shorten the time between chemotherapy treatments, large numbers of progenitor and immature blood cells could be given back to the patient. This would have the effect of greatly reducing the time the patient would have low blood cell counts, thereby allowing more rapid resumption of the chemotherapy treatment. The longer chemotherapy is given and the shorter the duration between treatments, the greater the odds of successfully killing the cancer.

The hematopoietic cells required for progenitor cell expansion may come from either bone marrow withdrawal or peripheral blood collection. Bone marrow harvests would result in collection of approximately $4 \times 10^5$ CFU-GM progenitor cells. Phoresis of 5 liters of peripheral blood would collect approximately $10^5$ CFU-GM although this number could be increased to $10^6$ CFU-GM by prior treatment of the donor with GM-CSF. Rapid recovery of a patient would require transfusion of approximately $1 \times 10^8$ to $5 \times 10^8$ CFU-GM. Therefore, expansion of bone marrow or peripheral blood to increase the number of CFU-GM would be of benefit to chemotherapy administration and cancer treatment.

Gene therapy is a rapidly growing field in medicine which is also of inestimable clinical potential. Gene therapy is, by definition, the insertion of genes into cells for the purpose of medicinal therapy. Research in gene therapy has been on-going for several years in several types of cells in vitro and in animal studies, and has recently entered the first human clinical trials. Gene therapy has many potential uses in treating disease and has been reviewed extensively. See, e.g., Boggs, *Int. J. Cell Cloning.* (1990) 8:80–96, Kohn et al, *Cancer Invest.* (1989) 7 (2):179–192, Lehn, *Bone Marrow Transp.* (1990) 5:287–293, and Verma, *Scientific Amer.* (1990) pp. 68–84.

The human hematopoietic system is an ideal choice for gene therapy in that hematopoietic stem cells are readily accessible for treatment (bone marrow or peripheral blood harvest), they are believed to posses unlimited self-renewal capabilities (inferring lifetime therapy), and upon reinfusion, can expand and repopulate the marrow. Unfortunately, achieving therapeutic levels of gene transfer into stem cells has yet to be accomplished in humans.

Several disorders of the hematopoietic system include thalassemia, sickle cell anemia, Falconi's anemia, acquired immune deficiency syndrome (AIDS) and SCIDS (ADA, adenosine deaminase deficiency). These candidates include both diseases that are inherited such as hemoglobinopathies and virally caused diseases of the hematopoietic system such as AIDS.

A salient problem which remain to be addressed for successful human gene therapy is the ability to insert the desired therapeutic gene into the chosen cells in a quantity such that it will be beneficial to the patient. To date, no method for doing this is available.

There is therefore a considerable need for methods and compositions for the in vitro replication of human stem cells and for the optimization of human hematopoietic progenitor cell cultures, particularly in light of the great potential for stem cell expansion, progenitor cell expansion, and gene therapy offered by these systems. Unfortunately, to date, attempts to achieve such results have been disappointing.

An in vitro system that permitted the controlled production of specific lineages of blood cells from within a hematopoietic cell population would have many applications. Controlled production of red blood cells would permit the in vitro production of red blood cell units for clinical replacement (transfusion) therapy. As is well known, red cells transfused are used in the treatment of anemia following elective surgery, in cases of traumatic blood loss, and in the supportive care of, e.g., cancer patients. Similarly, controlled production of platelets would permit the in vitro production of platelets for platelet transfusion therapy, for example for cancer patients in whom thrombocytopenia is caused by chemotherapy. For both red cells and platelets, current volunteer donor pools are accompanied by the risk of infectious contamination, and availability of an adequate supply can be limited. Controlled in vitro production of specified lineage of mature blood cells circumvent these problems.

Controlled, selective depletion of a particular lineage of cells from within a hematopoietic cell population can similarly confer important advantages. For example, production of stem cells and myeloid cells while selectively depleting T-cells from a bone marrow cell population could be very important for the management of patients with human immunodeficiency virus (HIV) infection. Since the major reservoir of HIV is the pool of mature T-cells, selective irradication of the mature T-cells from a hematopoietic cell mass collected from a patient has considerable potential therapeutic benefit. If one could selectively remove all the mature T-cells from within an HIV infected bone marrow cell population while maintaining viable stem cells, the T-cell depleted bone marrow sample could then be used to "rescue" the patient following hematolymphoid ablation and autologous bone marrow transplantation. Although there are reports of the isolation of progenitor cells (see, e.g., U.S. Pat. No. 5,061,620 as representative) such techniques are distinct from and should not be confused with the selective removal of T-cells from a hematopoietic tissue culture.

Another application of T-cell depletion is the prevention of graft-versus-host disease (GVHD) in allogeneic bone marrow transplantation. GVHD is a major limiting factor in the success of allogeneic bone marrow transplantation. Depletion of T-cells from a stem/progenitor cell population prior to allogeneic transplant would directly reduce the incidence and severity of GVHD. This depletion in turn would greatly decrease the morbidity and mortality of allogeneic bone marrow transplantation. While there are currently many techniques available for depleting T-cells from bone marrow samples (see e.g. Antin, J. H. et al, *Blood*, vol. 78, pp. 2139–2149 (1991)) none of these techniques allow the concurrent expansion of the hematopoietic progenitor cell population. Thus all of the previously developed techniques result in a diminution in the ability of the bone marrow sample to successfully engraft, thereby resulting in an increased incidence of graft failure. There is accordingly a considerable need for a method for depleting T-cells from a human hematopoietic mononuclear cell population, while maintaining or increasing the hematopoietic progenitor cell pool within the hematopoietic cell sample.

In addition, if it were possible to establish a functioning in vitro human tissue system, one could then utilize such a system as a model to stude the effects of chemical substances and/or physical conditions on a human hematopoietic cell mass or the hematopoietic process itself. Thus, by culturing such a system in the presence of a selected chemical substance and/or physical condition and comparing the state of the culture (total cell population, relative abundance of particular cell type, concentration of cell products in growth medium, etc.) with that of an identical culture, cultured in the absence of the selected chemical substance and/or physical condition, it would be possible to ascertain the effect of the selected chemical substance and/or physical condition on the hematopoietic cell mass or the hematopoietic process. In this way, such a functioning in vitro human tissue system could be utilized in an assay to detect the effect of a chemical substance and/or physical condition on a human hematopoietic cell mass or the hematopoietic process itself.

A further application of selective cell removal is the purging of malignant cells from bone marrow cultures for autologous bone marrow transplantation of cancer patients in which the cancer has metastasized. If it were possible to maintain a viable and producted human hematopoietic in vitro culture under conditions, which would lead to the depletion and extinction of malignant cells, then one could utilize such a culture for an autologous bone marrow transplant after a bout of chemotherapy, without the consequence of reintroducing metastasized malignant cells to the patient via the bone marrow transplant.

Thus, there remains a need for a functioning in vitro human hematopoietic tissue system and methods and conditions for maintaining such a system.

SUMMARY OF THE INVENTION

Accordingly, it is an object of this invention to provide novel methods, including culture media conditions, for the in vitro replication of human stem cells.

It is another object of this invention to provide novel methods, including culture media conditions, for the optimization of human hematopoietic progenitor cell cultures.

It is another object of the present invention to provide a novel, functioning, in vitro hematopoietic tissue system which may serve as a model of hematopoiesis.

It is another object of the present invention to provide a novel, functioning, in vitro hematopoietic tissue system which is substantially free of T-cells and B-cells.

It is another object of the present invention to provide a novel, functioning, in vitro hematopoietic tissue system in which at least a portion of the stem cells present have been genetically transformed.

It is another object of this invention to provide a novel, functioning, in vitro bone marrow tissue system in which the lineages of blood cells, including stem cells, produced can be controlled.

It is another object of this invention to provide novel methods, including culture media conditions, for the optimization of human hematopoietic progenitor cell cultures and to control the lineage composition of the mature cells produced.

It is another object of the present invention to provide novel methods, including culture media conditions, for the optimization of human hematopoietic progenitor cell cultures and to control the linage composition of the mature cells produced, in which at least a portion of the mature cells are derived from stem cells which have been genetically transformed.

It is another object of this invention to provide novel methods, including culture media conditions, for the selective enhanced production of red blood cells.

It is another object of this invention to provide novel methods, including culture media conditions, for the depletion of T-cells and B-cells from a human hematopoietic cell population.

It is another object of this invention to provide novel methods, including culture media conditions, for removing malignant cells from human hematopoietic cell population.

It is another object of this invention to provide novel methods, including culture media conditions, for assaying the affect of a substance or substances on a human replicating hematopoietic cell population.

It is another object of the present invention to provide novel methods, including culture media conditions, for assaying the effect of a physical condition or conditions on a human replicating hematopoietic cell population.

It is another object of the present invention to provide novel methods, including culture media conditions, for assaying the effect of genetic transformation of stem cells on a human replicating hematopoietic cell population.

It is another object of the present invention to provide novel methods for performing bone marrow transplantation in which the bone marrow tissue implanted in a patient is obtained according to the present method.

It is another object of the present invention to provide novel methods for performing bone marrow transplantation in which the bone marrow tissue implanted in a patient has been depleted of T-cells and B-cells.

It is another object of the present invention to provide novel methods for performing bone marrow transplantation in which the bone marrow tissue implanted in a patient has been depleted of malignant cells.

It is another object of the present invention to provide novel methods for performing bone marrow transplantation in which the bone marrow tissue implanted in a patient has been enriched in the population of a particular cell type as compared to the total cell population.

It is another object of the present invention to provide novel methods for performing bone marrow transplantation in which the bone marrow tissue implanted in a patient comprises stem cells which have been genetically transformed.

The present invention is based on the inventors' discovery of novel methods, including culture media conditions, which provide for in vitro human stem cell division and/or the optimization of human hematopoietic progenitor cell cultures. These methods rely on culturing human stem cells and/or human hematopoietic progenitor cells in a liquid culture medium which is replaced, preferably perfused, either continuously, periodically, or intermittently, at a rate of 1 milliliter (ml) of medium per ml of culture per about 24 to about 48 hour period, and removing metabolic products and replenishing depleted nutrients while maintaining the culture under physiologically acceptable conditions. In a particularly preferred embodiment of the present invention, the above medium replacement rate is used in conjunction with the addition of hematopoietic growth factors to the rapidly exchanged culture medium.

The inventors have discovered that the increased medium exchange rate used in accordance with the present invention, with the optional addition of hematopoietic growth factors to the rapidly exchanged culture medium, surprisingly (1) supports cultures in which human stem cells proliferate over extended periods of time of at least 5 months, (2) supports cultures in which human hematopoietic progenitor cells are produced by division and differentiation of human stem cells through extended culture periods of at least 5 months, (3) stimulates the increased metabolism of and growth factor, including GM-CSF, secretion from human stromal cells, including human bone marrow stromal cells, 4) provides for the depletion of T-cells and B-cells from a human hematopoietic mononuclear cell population, (5) provides a method for assaying the affect of a substance or substances or physical conditions on a human hematopoietic cell population, (6) provides for the depletion of malignant cells from a human hematopoietic cell population, and (7) supports cultures in which human stem cells continue to divide over long periods of time and, thus, may be genetically transformed with a suitable vector such as a retrovirus. The present invention provides, for the first time, human stem cell survival and proliferation in culture. In addition, the present invention provides a functioning human in vitro tissue system which may serve as a model for a human hematopoietic cell mass of the process of hematopoiesis.

DESCRIPTION OF THE PREFERRED EMBODIMENTS

The advantages of the present invention may be observed whenever the present invention is applied to any standard system for liquid human hematopoietic culture. By the use of the rapid medium exchange rates used in accordance with the present invention, with the optional addition of supplementary hemotopoietic growth factors to the culture, the inventors have suprisingly discovered that one is able to make standard systems for liquid human hematopoietic cultures, which comprises cultures performed in the presence or absence of animal sera or plasmas, including horse, calf, fetal calf, or human serum, perform in a qualitatively superior manner. Human liquid hematopoietic cultures which may be used in accordance with the invention can be performed at cell densities of from $10^4$ to $5 \times 10^8$ cells per ml of culture, using standard known medium components such as, for example, IMDM, MEM, DMEM, RPMI 1640, Alpha Medium or McCoy's Medium, which can use combinations of serum albumin, cholesterol and/or insulin, transferrin, lecithin, selenium and inorganic salts. As known, these cultures may be supplemented with corticosteriods, such as hydrocortisone at a concentration of $10^{-4}$ to $10^{-7}$ M, or other corticosteriods at equal potent dose such as cortisone, dexamethasone or Solu-Medrol® (Upjohn).

These cultures are typically carried out at a pH which is roughly physiologic, i.e. 6.9 to 7.6. The medium is kept at an oxygen concentration that corresponds to an oxygen-containing atmosphere which contains from 1 to 20 vol. percent oxygen, preferably 3 to 12 vol. percent oxygen. The preferred range of $O_2$ concentration refers to the concentration of $O_2$ near the cells, not necessarily at the point of $O_2$ introduction which may be at the medium surface or through a membrane. Using these standard culture techniques, the cell mass used may be enriched, by any desired amount, such as by up to $10^3$ fold or more, either for stem cell content or for hematopoietic progenitor cell content. Different known methods may be used to achieve this enrichment, corresponding either to a negative selection method or a positive selection method. For example, in accordance with the negative selection method, mature cells are removed using immunological techniques, e.g., labelling non-progenitor, non-stem cells with a panel of mouse anti-human monoclonal antibodies, then removing the mouse antibody-coated cells by adherence to rabbit-anti-mouse Ig-coated plastic dishes. See e.g., *Emerson et al, J. Clin. Invest.* (1985) 76:1286–1290. Via such procedures, stem cells and progenitor cells may be concentrated to any degree desired.

The present invention relies on a fundamental alteration of the conditions of liquid human bone marrow cultures under any of the above conditions; rapid replacement of the nutrient medium. Standard culture schedules call for medium and serum to be exchanged weekly, either as a single exchange performed weekly or a one-half medium and serum exchange performed twice weekly. In accordance with the present invention, the nutrient medium of the culture is replaced, preferably perfused, either continuously or periodically, at a rate of about 1 ml per ml or culture per about 24 to about 48 hour period, for cells cultured at a density of from $2 \times 10^6$ to $1 \times 10^7$ cells per ml. For cell densities of from $1 \times 10^4$ to $2 \times 10^{6}$ cells per ml the same medium exchange rate may be used. Thus, for cell densities of about $10^7$ cells per ml, the present medium replacement rate may be expressed as 1 ml of medium per $10^7$ cells per about 24 to about 48 hour period. For cell densities higher than $10^7$ cells per ml, the medium exchange rate may be increased proportionality to achieve a constant medium and serum flux per cell per unit time. Replacement of the nutrient medium in accordance with the invention may be carried out in any manner which will achieve the result of replacing the medium, e.g., by removing an aliquot of spent culture medium and replacing it with a fresh aliquot. The flow of the aliquot being added may be by gravity, by pump, or by any other suitable means, such as syringe or pipette. The flow may be in any direction or multiplicity or directions, depending upon the configuration and packing of the culture. Preferably, the new medium is added to the culture in a manner such that it contacts the cell mass. Most preferably, it is added to the culture in a manner mimicking in vivo perfusion, i.e., it is perfused through at least part of the cell mass and up to the whole cell mass.

Another, optional but important, embodiment of the present invention, resides in the addition of the hematopoietic growth factors to the rapidly exchanged cultures. In a particularly preferred aspect of this embodiment, the cytokines IL-3 and GM-CSF are both added, together, to the medium at a rate of from 0.1 to 100 ng/ml/day, preferably about 0.5 to 10 ng/ml/day, most preferably 1 to 2 ng/ml/day. Epo may be added to the nutrient medium in an amount of from 0.001 to 10 U/ml/day, preferably 0.05 to 0.15 U/ml/day. Mast cell growth factor (MCF, c-kit ligand, Steel factor), may be added to the medium in an amount of from 1 to 100 ng/ml/day, preferably 10 to 50 ng/ml/day. IL-1 ($\alpha$ or $\beta$) may also be added in an amount of from 10 to 100 units/ml per 3 to 5 day period. Additionally, IL-6, G-CSF, basic fibroblast growth factor, IL-7, IL-8, IL-9, IL-10, IL-11, PDGF, or EGF may be added, at a rate of from 1 to 100 ng/ml/day.

The metabolic product level in the medium is normally maintained within a particular range. Glucose concentration is usually maintained in the range of about 5 to 20 mM. Lactate concentration is generally maintained in the range of from about 1 to 3 mM. Ammonium concentration is usually maintained below about 2.4 mM. These concentrations can be monitored by either periodic off line or on line continuous measurements using known methods. See, e.g., *Caldwell et al, J. Cell Physiol.* (1991) 147:344–353. The cells which may be cultured in accordance with the present invention may be human peripheral blood mononuclear cells, human bone marrow cells, human fetal liver cells, human cord blood cells, and/or human spleen cells. Each of these cell masses contains human stem cells and human hematopoietic progenitor cells.

In a preferred embodiment of the invention, the cell culture may be enriched to augment the human stem cell content of the cell mass. Such enrichment may achieved as described above, and, when used in accordance with the invention, provides the first useful means for genetic therapy via gene transfer into human bone marrow stem cells. In this embodiment, a packing cell line infected with a retrovirus, or a supernatant obtained from such a packaging cell line culture, is added to human stem cells cultured in accordance with the invention to obtain transformed human bone marrow stem cells. Such genetic transformation of human stem cells may be carried out an described in U.S. Pat. application Ser. No. 07/740,590 filed Aug. 5, 1991, now U.S. Pat. No. 5,399,493, which is incorporated herein by reference. The present invention provides increased levels of stem cell and human hematopoietic progenitor cell replication, whereas, by contrast, prior cultures provided only for human hematopoietic progenitor cell replication at a decreasing rate (i.e., decaying cultures). The present culture system provides, for the first time, expansion of cells in culture, which is required for retroviral infection was carried out on decaying cultures provided no infection of earlier cells. The preset invention, particularly when it is practiced together with an enriched stem cell pool, and even more particularly when it is practiced still further with the use of hematopoietic growth factors, provides a very effective means for obtaining stem cell infection in vitro.

In accordance with the present invention one obtains cultures in which human hematopoietic progenitor cells are produced by division and differentiation from human stem cells throughout a culture period of at least five months. That is, one obtains a culture which supports stem cell survival and proliferation in culture.

Data obtained by the inventors indicates that medium perfusion rate is a very significant variable in determining the behavior of in vitro human bone marrow cultures. This data shows that when the medium exchange rate is increase from the traditional once per week Dexter rate to a daily medium exchange rate of 7 volumes per week, a significant effect on in vitro hematopoiesis is obtained. In experiments carried out by the inventors, all cultures displayed a significant loss of cells during the first 3 to 4 weeks. Following this decay, the cultures stabilized and the effect of a medium perfusion rate became more pronounced.

A 3.5 per week medium exchange rate led to the most prolific cultures in the absence of added growth factors and also to cultures of greatest longevity in terms of progenitor cell production. Of particular note, during weeks 4 to 10, the biweekly number of nonadherent cells produced was actually stable or increasing.

Over the entire course of the cultures, the cumulative number of cells produced after week 3.5 was almost three-fold greater than that which is produced under the traditional Dexter culture protocol. Further, stable production of progenitor cells is maintained until week 18.

Bone marrow stomal cells may or may not be present in the cultures of the invention. In typical cultures, stromal cells are present in the cell culture in an amount of approximately $10^{-3}$ to $10^{-1}$ (stromal cells/total cells).

In another aspect of the invention, the inventors discovered that the cultures of the invention surprisingly provide increased metabolism and GM-CSF and IL-6 secretion from human bone marrow stromal cells. Whereas no GM-CSF is detected in human bone marrow stromal cells supernatant, rapid medium exchange in accordance with the invention stimulates human bone marrow stromal cells to secrete 300 femtograms/ml/day to 200 picograms/ml/day of GM-CSF. Secretion of IL-6 by human bone marrow stromal cells is also increased by rapid medium exchange in accordance with the invention from 1 to 2 ng/ml/day to 2 to 4 ng/ml/day. This increase is observed both when only the rapid medium exchange rate of the invention is used, and when the rapid exchange rate together with the addition of hematopoietic growth factors is used. On the basis of data obtained by the inventors, the effect of the rapid medium exchange rates of the invention on human stromal cell production of cytokines should be observed with human stromal cells in any complex tissue culture system.

Illustratively, the medium used in accordance with the invention may comprise three basic components. The first component is a media component comprised of IMDM, MEM, DMEM, RPMI 1640, Alpha Medium or McCoy's Medium, or an equivalent known culture medium component. The second is a serum component which comprises at least horse serum or human serum and may optionally further comprise fetal calf serum, newborn calf serum, and/or calf serum. The third component is a corticosteriod, such as hydrocortisone, cortisone, dexamethasone, Solu-Medrol® (Upjohn), or a combination of these, preferably hydrocortisone. The serum component can be replaced in whole or in part with any standard serum replacement mixture.

The compositional make up of various media which can be used are set forth below.

| | Dulbecco's[1] Modified Eagle Media (D-MEM) | | | | | | | | | | | | | |
|---|---|---|---|---|---|---|---|---|---|---|---|---|---|---|
| COMPONENT | 320-1885 1X Liquid mg/L | 380-2320 1X Liquid mg/L | 430-1600 Powder mg/L | 320-1965 1X Liquid mg/L | 380-2430 1X Liquid mg/L | 430-2100 Powder mg/L | 430-2800 Powder mg/L | 430-3000 Powder mg/L | 320-1960 1X Liquid mg/L | 320-1970 1X Liquid mg/L | 320-1995 1X Liquid mg/L | 430-3700 Powder mg/L | 326-1968 1X Liquid mg/L | 430-3000 Powder mg/L |
| INORGANIC SALTS: | | | | | | | | | | | | | | |
| $CaCl_2$ (anhyd.) | 200.00 | 200.00 | 200.00 | 200.00 | 200.00 | 200.00 | 200.00 | 200.00 | 200.00 | 200.00 | 200.00 | 200.00 | 200.00 | 200.00 |
| $Fe(NO_3)_3 \cdot 9H_2O$ | 0.10 | 0.10 | 0.10 | 0.10 | 0.10 | 0.10 | 0.10 | 0.10 | 0.10 | 0.10 | 0.10 | 0.10 | 0.10 | 0.10 |
| KCl | 400.00 | 400.00 | 400.00 | 400.00 | 400.00 | 400.00 | 400.00 | 400.00 | 400.00 | 400.00 | 400.00 | 400.00 | 400.00 | 400.00 |
| $MgSO_4$ (anhyd.) | — | — | 97.67 | — | — | 97.67 | 97.67 | 97.67 | — | — | — | 97.67 | — | 97.67 |
| $MgSO_4 \cdot 7H_2O$ | 200.00 | 200.00 | — | 200.00 | 200.00 | — | — | — | 200.00 | 200.00 | 200.00 | — | 200.00 | — |
| NaCl | 6400.00 | 4750.00 | 6400.00 | 6400.00 | 4750.00 | 6400.00 | 6400.00 | 6400.00 | 6400.00 | 6400.00 | 6400.00 | 4750.00 | 6400.00 | 6400.00 |
| $NaHCO_3$ | 3700.00 | 3700.00 | — | 3700.00 | 3700.00 | — | — | — | 3700.00 | 3700.00 | 3700.00 | — | 3700.00 | — |
| $NaH_2PO_4 \cdot H_2O$[a] | 125.00 | 125.00 | 125.00 | 125.00 | 125.00 | 125.00 | 125.00 | 125.00 | 125.00 | 125.00 | 125.00 | 125.00 | 125.00 | 125.00 |
| OTHER COMPONENTS: | | | | | | | | | | | | | | |
| D-Glucose | 1000.00 | 1000.00 | 1000.00 | 4500.00 | 4500.00 | 4500.00 | 4500.00 | 4500.00 | 4500.00 | 4500.00 | 4500.00 | 4500.00 | 4500.00 | — |
| Phenol red | 15.00 | 15.00 | 15.00 | 15.00 | 15.00 | 15.00 | 15.00 | — | 15.00 | — | 15.00 | 15.00 | 15.00 | — |
| HEPES | — | 5958.00 | — | — | 5958.00 | — | — | — | — | — | — | 5958.00 | — | — |
| Sodium pyruvate | 110.00 | 110.00 | 110.00 | — | — | — | 110.00 | — | — | — | 110.00 | — | — | — |
| AMINO ACIDS: | | | | | | | | | | | | | | |
| L-Arginine.HCl | 84.00 | 84.00 | 84.00 | 84.00 | 84.00 | 84.00 | 84.00 | 84.00 | 84.00 | 84.00 | 84.00 | 84.00 | 84.00 | 84.00 |
| L-Cystine | 48.00 | 48.00 | — | 48.00 | 48.00 | — | — | — | 48.00 | 48.00 | 48.00 | — | 48.00 | — |
| L-Cystine.2HCl | — | — | 62.57 | — | — | 62.57 | 62.57 | 62.47 | — | — | — | 62.57 | — | 62.57 |
| L-Glutamine | 584.00 | 584.00 | 584.00 | 584.00 | 584.00 | 584.00 | 584.00 | 584.00 | — | — | 584.00 | 584.00 | 584.00 | — |
| Glycine | 30.00 | 30.00 | 30.00 | 30.00 | 30.00 | 30.00 | 30.00 | 30.00 | 30.00 | 30.00 | 30.00 | 30.00 | 30.00 | 30.00 |
| L-Histidine.HCl.$H_2O$ | 42.00 | 42.00 | 42.00 | 42.00 | 42.00 | 42.00 | 42.00 | | | | | | | |
| L-Isoleucine | 105.00 | 105.00 | 105.00 | 105.00 | 105.00 | 105.00 | 105.00 | | | | | | | |
| L-Leucine | 105.00 | 105.00 | 105.00 | 105.00 | 105.00 | 105.00 | 105.00 | | | | | | | |
| L-Lysine.HCl | 146.00 | 146.00 | 146.00 | 146.00 | 146.00 | 146.00 | 146.00 | | | | | | | |
| L-Methionine | 30.00 | 30.00 | 30.00 | 30.00 | 30.00 | 30.00 | 30.00 | | | | | | | |
| L-Phenylalanine | 66.00 | 66.00 | 66.00 | 66.00 | 66.00 | 66.00 | 66.00 | | | | | | | |
| L-Serine | 42.00 | 42.00 | 42.00 | 42.00 | 42.00 | 42.00 | 42.00 | | | | | | | |
| L-Threonine | 95.00 | 95.00 | 95.00 | 95.00 | 95.00 | 95.00 | 95.00 | | | | | | | |
| L-Tryptophan | 16.00 | 16.00 | 16.00 | 16.00 | 16.00 | 16.00 | 16.00 | | | | | | | |
| L-Tyrosine | 72.00 | 72.00 | — | 72.00 | 72.00 | — | — | | | | | | | |
| L-Tyrosine.2Na.$2H_2O$ | — | — | 103.79 | — | — | 103.79 | 103.79 | | | | | | | |
| L-Valine | 94.00 | 94.00 | 94.00 | 94.00 | 94.00 | 94.00 | 94.00 | | | | | | | |
| VITAMINS: | | | | | | | | | | | | | | |
| D-Ca pantothenate | 4.00 | 4.00 | 4.00 | 4.00 | 4.00 | 4.00 | 4.00 | | | | | | | |
| Choline chloride | 4.00 | 4.00 | 4.00 | 4.00 | 4.00 | 4.00 | 4.00 | | | | | | | |
| Folic acid | 4.00 | 4.00 | 4.00 | 4.00 | 4.00 | 4.00 | 4.00 | | | | | | | |
| i-Inositol | 7.20 | 7.20 | 7.20 | 7.20 | 7.20 | 7.20 | 7.20 | | | | | | | |
| Niacinamide | 4.00 | 4.00 | 4.00 | 4.00 | 4.00 | 4.00 | 4.00 | | | | | | | |
| Pyridoxal.HCl | 4.00 | 4.00 | 4.00 | 4.00 | 4.00 | 4.00 | 4.00 | | | | | | | |
| Riboflavin | 0.40 | 0.40 | 0.40 | 0.40 | 0.40 | 0.40 | 0.40 | | | | | | | |
| Thiamine.HCl | 4.00 | 4.00 | 4.00 | 4.00 | 4.00 | 4.00 | 4.00 | | | | | | | |

-continued

| Dulbecco's[1] Modified Eagle Media (D-MEM) | | | | | | | |
|---|---|---|---|---|---|---|---|
| L-Histidine.HCl.H$_2$O | 42.00 | 42.00 | 42.00 | 42.00 | 42.00 | 42.00 | 42.00 |
| L-Isoleucine | 105.00 | 105.00 | 105.00 | 105.00 | 105.00 | 105.00 | 105.00 |
| L-Leucine | 105.00 | 105.00 | 105.00 | 105.00 | 105.00 | 105.00 | 105.00 |
| L-Lysine.HCl | 146.00 | 146.00 | 146.00 | 146.00 | 146.00 | 146.00 | 146.00 |
| L-Methionine | 30.00 | 30.00 | — | 30.00 | 30.00 | 30.00 | 30.00 |
| L-Phenylalanine | 66.00 | 66.00 | 66.00 | 66.00 | 66.00 | 66.00 | 66.00 |
| L-Serine | 42.00 | 42.00 | 42.00 | 42.00 | 42.00 | 42.00 | 42.00 |
| L-Threonine | 95.00 | 95.00 | 95.00 | 95.00 | 95.00 | 95.00 | 95.00 |
| L-Tryptophan | 16.00 | 16.00 | 16.00 | 16.00 | 16.00 | 16.00 | 16.00 |
| L-Tyrosine | — | 72.00 | 72.00 | 72.00 | — | 72.00 | — |
| L-Tyrosine.2Na.2H$_2$O | 103.79 | — | — | — | 103.79 | — | 103.79 |
| L-Valine | 94.00 | 94.00 | 94.00 | 94.00 | 94.00 | 94.00 | 94.00 |
| VITAMINS: | | | | | | | |
| D-Ca pantothenate | 4.00 | 4.00 | 4.00 | 4.00 | 4.00 | 4.00 | 4.00 |
| Choline chloride | 4.00 | 4.00 | 4.00 | 4.00 | 4.00 | 4.00 | 4.00 |
| Folic acid | 4.00 | 4.00 | 4.00 | 4.00 | 4.00 | 4.00 | 4.00 |
| i-Inositol | 7.20 | 7.20 | 7.20 | 7.20 | 7.20 | — | 7.20 |
| Niacinamide | 4.00 | 4.00 | 4.00 | 4.00 | 4.00 | 4.00 | 4.00 |
| Pyridoxal.HCl | 4.00 | 4.00 | 4.00 | 4.00 | 4.00 | 4.00 | 4.00 |
| Riboflavin | 0.40 | 0.40 | 0.40 | 0.40 | 0.40 | 0.40 | 0.40 |
| Thiamine.HCl | 4.00 | 4.00 | 4.00 | 4.00 | 4.00 | 4.00 | 4.00 |

[1]Dulbecco, R. and Freeman, G. (1959) Virology 8, 396. Smith, J. D., Freeman, G., Vogt, M., and Dulbecco, R. (1960) Virology 12, 185. Tissue Culture Standards Committee, In Vitro 6:2, 93.
[a]Values shown are in conformance with the Tissue Culture Standards Committee, In Vitro (1970) 9:6.

| | DMEM/F12 | | | |
|---|---|---|---|---|
| COMPONENT | 320-1330 1X Liquid mg/L | 430-2400 Powder mg/L | 320-1320 1X Liquid mg/L | 430-2900 Powder mg/L |
| INORGANIC SALTS: | | | | |
| CaCl$_2$ (anhyd.) | 116.60 | 116.60 | 116.60 | 116.60 |
| CuSO$_4$.5H$_2$O | 0.0013 | 0.0013 | 0.0013 | 0.0013 |
| Fe(NO$_3$)$_3$.9H$_2$O | 0.05 | 0.05 | 0.05 | 0.05 |
| FeSO$_4$.7H$_2$O | 0.417 | 0.417 | 0.417 | 0.417 |
| KCl | 311.80 | 311.80 | 311.80 | 311.80 |
| MgCl$_2$ | — | 28.64 | 28.64 | 28.64 |
| MgCl$_2$.6H$_2$O | 61.00 | — | — | — |
| MgSO$_4$ | — | 48.84 | 48.84 | 48.84 |
| MgSO$_4$.7H$_2$O | 100.00 | — | — | — |
| NaCl | 6999.50 | 6999.50 | 6999.50 | 6999.50 |
| NaHCO$_3$ | 1200.00 | — | 2438.00 | — |
| NaH$_2$PO$_4$.H$_2$O | 62.50 | 62.50 | 62.50 | 62.50 |
| Na$_2$HPO$_4$ | — | 71.02 | 71.02 | 71.02 |
| Na$_2$HPO$_4$.7H$_2$O | 134.00 | — | — | — |
| ZnSO$_4$.7H$_2$O | 0.432 | 0.432 | 0.432 | 0.432 |
| OTHER COMPONENTS: | | | | |
| D-Glucose | 3151.00 | 3151.00 | 3151.00 | 3151.00 |
| HEPES | 3574.50 | 3574.50 | — | — |
| Na Hypoxanthine | 2.39 | 2.39 | 2.39 | 2.39 |
| Linoleic acid | 0.042 | 0.042 | 0.042 | 0.042 |
| Lipoic acid | 0.105 | 0.105 | 0.105 | 0.105 |
| Phenol red | 8.10 | 8.10 | 8.10 | 8.10 |
| Putreacine.2HCl | 0.081 | 0.081 | 0.081 | 0.081 |
| Sodium pyruvate | 55.00 | 55.00 | 55.00 | 55.00 |
| AMINO ACIDS: | | | | |
| L-Alanine | 4.45 | 4.45 | 4.45 | 4.45 |
| L-Arginine HCl | 147.50 | 147.50 | 147.50 | 147.50 |
| L-Asparagine.H$_2$O | 7.50 | 7.50 | 7.50 | 7.50 |
| L-Aspartic acid | 6.65 | 6.65 | 6.65 | 6.65 |
| L-Cysteine.HCl.H$_2$O | 17.56 | 17.56 | 17.56 | 17.56 |
| L-Cystine.2HCl | 31.29 | 31.29 | 31.29 | 31.29 |
| L-Glutamic acid | 7.35 | 7.35 | 7.35 | 7.35 |
| L-Glutamine | 365.00 | 365.00 | 365.00 | 365.00 |
| Glycine | 18.75 | 18.75 | 18.75 | 18.75 |
| L-Histidine.HCl.H$_2$O | 31.48 | 31.48 | 31.48 | 31.48 |
| L-Isoleucine | 54.47 | 54.47 | 54.47 | 54.47 |
| L-Leucine | 59.05 | 59.05 | 59.05 | 59.05 |
| L-Lysine.HCl | 91.25 | 91.25 | 91.25 | 91.25 |
| L-Methionine | 17.24 | 17.24 | 17.24 | 17.24 |
| L-Phenylalanine | 35.48 | 35.48 | 35.48 | 35.48 |
| L-Proline | 17.25 | 17.25 | 17.25 | 17.25 |
| L-Serine | 26.25 | 26.25 | 26.25 | 26.25 |
| L-Threonine | 53.45 | 53.45 | 53.45 | 53.45 |
| L-Tryptophan | 9.02 | 9.02 | 9.02 | 9.02 |
| L-Tyrosine.2Na.2H$_2$O | 55.79 | 55.79 | 55.79 | 55.79 |
| L-Valine | 52.85 | 52.85 | 52.85 | 52.85 |
| VITAMINS: | | | | |
| Biotin | 0.0035 | 0.0035 | 0.0035 | 0.0035 |
| D-Ca pantothenate | 2.24 | 2.24 | 2.24 | 2.24 |
| Choline chloride | 8.98 | 8.98 | 8.98 | 8.98 |
| Folic acid | 2.65 | 2.65 | 2.65 | 2.65 |
| i-Inositol | 12.60 | 12.60 | 12.60 | 12.60 |
| Niacinamide | 2.02 | 2.02 | 2.02 | 2.02 |
| Pyridoxal.HCl | 2.00 | 2.00 | 2.00 | 2.00 |
| Pyridoxine.HCl | 0.031 | 0.031 | 0.031 | 0.031 |
| Riboflavin | 0.219 | 0.219 | 0.219 | 0.219 |
| Thiamine.HCl | 2.17 | 2.17 | 2.17 | 2.17 |
| Thymidine | 0.365 | 0.365 | 0.365 | 0.365 |
| Vitamin B$_{12}$ | 0.68 | 0.68 | 0.68 | 0.68 |

| Iscove's Modified Dulbecco's Media (IMDM)[1,2,3] | | |
|---|---|---|
| | 380-2440 | 430-2200 |
| | 1X Liquid | Powder |
| COMPONENT | mg/L | Mg/L |
| INORGANIC SALTS: | | |
| $CaCl_2$ (anhyd.) | 165.00 | 165.00 |
| KCl | 330.00 | 330.00 |
| $KNO_3$ | 0.076 | 0.076 |
| $MgSO_4$ (anhyd.) | 97.67 | 97.67 |
| NaCl | 4505.00 | 4505.00 |
| $NaHCO_3$ | 3024.00 | — |
| $NaH_2PO_4.H_2O$[a] | 125.00 | 125.00 |
| $Na_2SeO_3 5H_2O$ | 0.0173 | 0.0173 |
| OTHER COMPONENTS: | | |
| D-Glucose | 4500.00 | 4500.00 |
| Phenol red | 15.00 | 15.00 |
| HEPES | 5958.00 | 5958.00 |
| Sodium pyruvate | 110.00 | 110.00 |
| AMINO ACIDS: | | |
| L-Alanine | 25.00 | 25.00 |
| L-Asparagine.$H_2O$ | 28.40 | 28.40 |
| L-Arginine.HCl | 84.00 | 84.00 |
| L-Aspartic acid | 30.00 | 30.00 |
| L-Cystine.2HCl | 91.24 | 91.24 |
| L-Glutamic acid | 75.00 | 75.00 |
| L-Glutamine | 584.00 | 584.00 |
| Glycine | 30.00 | 30.00 |
| L-Histidine.HCl.$H_2O$ | 42.00 | 42.00 |
| L-Isoleucine | 105.00 | 105.00 |
| L-Leucine | 105.00 | 105.00 |
| L-Lysine.HCl | 146.00 | 146.00 |
| L-Methionine | 30.00 | 30.00 |
| L-Phenylalanine | 66.00 | 66.00 |
| L-Proline | 40.00 | 40.00 |
| L-Serine | 42.00 | 42.00 |
| L-Threonine | 95.00 | 95.00 |
| L-Tryptophan | 16.00 | 16.00 |
| L-Tyrosine.2Na.2$H_2O$ | 103.79 | 103.79 |
| L-Valine | 94.00 | 94.00 |
| VITAMINS: | | |
| Biotin | 0.013 | 0.013 |
| D-Ca pantothenate | 4.00 | 4.00 |
| Choline chloride | 4.00 | 4.00 |
| Folic acid | 4.00 | 4.00 |
| i-Inositol | 7.20 | 7.20 |
| Niacinamide | 4.00 | 4.00 |
| Pyridoxal.HCl | 4.00 | 4.00 |
| Riboflavin | 0.40 | 0.40 |
| Thiamine.HCl | 4.00 | 4.00 |
| Vitamin $B_{12}$ | 0.013 | 0.013 |

[1] Dulbecco, R. and Freeman, G. (1959) Virology 8, 396. Smith, J. D., Freeman, G., Vogt, M., and Dulbecco, R. (1960) Virology 12, 185, Tissue Culture Standards Committee, In Vitro 6:2, 93.

[2] Iscove, N. N. and Melchers, F., J. Experimental Medicine 147, 923.

[a] Values shown are in conformance with Tissue Culture Standards Committee, In Vitro (1970) 9:6.

[3] Iscove, N. N., personal communication.

| McCoy's 5A Media (modified)[1,2,3] | | | | | | | | |
|---|---|---|---|---|---|---|---|---|
| | 330–6600 | 380–2330 | 430–1500 | 320–6608 | 320–6601[a] | 320–6610 | 320–6620 | 320–6630 |
| | 1X Liquid | 1X Liquid | Powder | 1X Liquid | 1X Liquid | 1X Liquid | 1X Liquid | 1X Liquid |
| COMPONENT | mg/L | mg/L | mg/L | mg/L | mg/L | mg/L | mg/L | mg/L |
| INORGANIC SALTS: | | | | | | | | |
| $CaCl_2$ (anhydr.) | 100.00 | 100.00 | 100.00 | — | 140.00 | 100.00 | 100.00 | 100.00 |
| KCl | 400.00 | 400.00 | 400.00 | 400.00 | 400.00 | 400.00 | 400.00 | 400.00 |
| $KH_2PO_4$ | — | — | — | — | 60.00 | — | — | — |
| $MgCl_2.6H_2O$ | — | — | — | — | 100.00 | — | — | — |
| $MgSO_4$ (anhydr.) | — | — | 97.67 | — | — | — | — | — |
| $MgSO_4.7H_2O$ | 200.00 | 200.00 | — | 200.00 | 100.00 | 200.00 | 200.00 | 200.00 |
| NaCl | 6460.00 | 5100.00 | 6460.00 | 6460.00 | 8000.00 | 6460.00 | 6460.00 | 6460.00 |
| $NaHCO_3$ | 2200.00 | 2200.00 | — | 2200.00 | 350.00 | 2200.00 | 2200.00 | 2200.00 |
| $NaH_2PO_4.H_2O$ | 580.00 | 580.00 | 580.00 | 1400.00 | — | 580.00 | 580.00 | 580.00 |
| $Na_2HPO_4.7H_2O$ | — | — | — | — | 90.00 | — | — | — |
| OTHER | | | | | | | | |

-continued

| COMPONENTS: | McCoy's 5A Media (modified)[1,2,3] | | | | | | | |
|---|---|---|---|---|---|---|---|---|
| Bacto-peptone | 600.00 | 600.00 | 600.00 | 600.00 | 600.00 | 600.00 | 600.00 | 600.00 |
| Fetal Bovine Serum | — | — | — | — | — | c | c | c |
| D-Glucose | 3000.00 | 30000.00 | 3000.00 | 3000.00 | 1000.00 | 3000.00 | 3000.00 | 3000.00 |
| Glutathione (reduced) | 0.50 | 0.50 | 0.50 | 0.50 | 0.50 | 0.50 | 0.50 | 0.50 |
| HEPES | — | 5958.00 | — | — | — | — | — | — |
| Phenol red | 10.00 | 10.00 | 10.00 | 10.00 | 10.00 | 10.00 | 10.00 | 10.00 |
| AMINO ACIDS: | | | | | | | | |
| L-Alanine | 13.90 | 13.90 | 13.90 | 13.90 | 13.90 | 13.90 | 13.90 | 13.90 |
| L-Arginine-HCl | 42.10 | 42.10 | 42.10 | 42.10 | 42.10 | 42.10 | 42.10 | 42.10 |
| L-Asparagine[a] | 45.00 | 45.00 | 45.00 | 45.00 | 45.00 | 45.00 | 45.00 | 45.00 |
| L-Aspartic acid | 19.97 | 19.97 | 19.97 | 19.97 | 19.97 | 19.97 | 19.97 | 19.97 |
| L-Cysteine[b] | 31.50 | 31.50 | 31.50 | 31.50 | 31.50 | 31.50 | 31.50 | 31.50 |
| L-Glutamic acid | 22.10 | 22.10 | 22.10 | 22.10 | 22.10 | 22.10 | 22.10 | 22.10 |
| L-Glutamine | 219.20 | 219.20 | 219.20 | 219.20 | 219.20 | 219.20 | 219.20 | 219.20 |
| Glycine | 7.50 | 7.50 | 7.50 | 7.50 | 7.50 | 7.50 | 7.50 | 7.50 |
| L-Histidine-HCl.H$_2$O | 20.96 | 20.96 | 20.96 | 20.96 | 20.96 | 20.96 | 20.96 | 20.96 |
| L-Hydroxyproline | 19.70 | 19.70 | 19.70 | 19.70 | 19.70 | 19.70 | 19.70 | 19.70 |
| L-Isoleucine | 39.36 | 39.36 | 39.36 | 39.36 | 39.36 | 39.36 | 39.36 | 39.36 |
| L-Leucine | 39.36 | 39.36 | 39.36 | 39.36 | 39.36 | 39.36 | 39.36 | 39.36 |
| L-Lysine-HCl | 36.50 | 36.50 | 36.50 | 36.50 | 36.50 | 36.50 | 36.50 | 36.50 |
| L-Methionine | 14.90 | 14.90 | 14.90 | 14.90 | 14.90 | 14.90 | 14.90 | 14.90 |
| L-Phenylalanine | 16.50 | 16.50 | 16.50 | 16.50 | 16.50 | 16.50 | 16.50 | 16.50 |
| L-Proline | 17.30 | 17.30 | 17.30 | 17.30 | 17.30 | 17.30 | 17.30 | 17.30 |
| L-Serine | 26.30 | 26.30 | 26.30 | 26.30 | 26.30 | 26.30 | 26.30 | 26.30 |
| L-Threonine | 17.90 | 17.90 | 17.90 | 17.90 | 17.90 | 17.90 | 17.90 | 17.90 |
| L-Tryptophan | 3.10 | 3.10 | 3.10 | 3.10 | 3.10 | 3.10 | 3.10 | 3.10 |
| L-Tyrosine | 18.10 | 18.10 | — | 18.10 | 18.10 | 18.10 | 18.10 | 18.10 |
| L-Tyrosine-2Na.2H$_2$O | — | — | 26.10 | — | — | — | — | — |
| L-Valine | 17.60 | 17.60 | 17.60 | 17.60 | 17.60 | 17.60 | 17.60 | 17.60 |
| VITAMINS; | | | | | | | | |
| Ascorbic acid | 0.50 | 0.50 | 0.50 | 0.50 | 0.50 | 0.50 | 0.50 | 0.50 |
| Biotin | 0.20 | 0.20 | 0.20 | 0.20 | 0.20 | 0.20 | 0.20 | 0.20 |
| Choline chloride | 5.00 | 5.00 | 5.00 | 5.00 | 5.00 | 5.00 | 5.00 | 5.00 |
| D-Ca pantothenate | 0.20 | 0.20 | 0.20 | 0.20 | 0.20 | 0.20 | 0.20 | 0.20 |
| Folic acid | 10.00 | 10.00 | 10.00 | 10.00 | 10.00 | 10.00 | 10.00 | 10.00 |
| l-Inositol | 36.00 | 36.00 | 36.00 | 36.00 | 36.00 | 36.00 | 36.00 | 36.00 |
| Niacinamide | 0.50 | 0.50 | 0.50 | 0.50 | 0.50 | 0.50 | 0.50 | 0.50 |
| Nicotinic acid | 0.50 | 0.50 | 0.50 | 0.50 | 0.50 | 0.50 | 0.50 | 0.50 |
| Para-aminobenzoic acid | 1.00 | 1.00 | 1.00 | 1.00 | 1.00 | 1.00 | 1.00 | 1.00 |
| Pyridoxal.HCl | 0.50 | 0.50 | 0.50 | 0.50 | 0.50 | 0.50 | 0.50 | 0.50 |
| Pyridoxine.HCl | 0.50 | 0.50 | 0.50 | 0.50 | 0.50 | 0.50 | 0.50 | 0.50 |
| Riboflavin | 0.20 | 0.20 | 0.20 | 0.20 | 0.20 | 0.20 | 0.20 | 0.20 |
| Thiamine.HCl | 0.20 | 0.20 | 0.20 | 0.20 | 0.20 | 0.20 | 0.20 | 0.20 |
| Vitamin B$_{12}$ | 2.00 | 2.00 | 2.00 | 2.00 | 2.00 | 2.00 | 2.00 | 2.00 |

[1]McCoy, T.A., Maxwell, M., and Kruse, P.F. (1959) Proc. Soc. Exper. Biol. Med. 100, 115.
[2]Hsu, T.C. and Kellogg, D.S., Jr. (1960) J. Nat. Cancer Inst. 25, 221.
[3]Iwakata, S. and Grace, J.T., Jr. (1964) N.Y.J. Med. 64:18, 2279.
[4]McCoy's 5A Medium formulated with Hanks' and Suspension Salts is a GIBCO modification and is not cited references 1–3.
[a]HCl form listed by the Tissue Culture Standards Commitee, In Vitro (1974) 9:6.
[b]Monohydrate form listed by the Tissue Culture Standards Commitee, In Vitro (1974) 9:6.
[c]Fetal Bovine Serum Supplementation:

| Cat. No. | FBS |
|---|---|
| 320–6610 | 10% v/v |
| 320-6620 | 20% v/v |
| 320-6630 | 30% v/v |

| F-10 Nutrient Mixture (Ham)[1] | | | | |
|---|---|---|---|---|
| COMPONENT | 320-1550 1X Liquid mg/L | 370-1955 10X Liquid mg/L | 380-3990 1X Liquid mg/L | 430-1300 Powder mg/L |
| INORGANIC SALTS: | | | | |
| $CaCl_2$ (anhyd.) | — | — | — | 33.29 |
| $CaCl_2.2H_2O$ | 44.10 | 441.00 | 44.10 | — |
| $CuSO_4.5H_2O$[a] | 0.0025 | 0.025 | 0.0025 | — |
| $FeSO_4.7H_2O$ | 0.834 | 8.34 | 0.834 | 0.834 |
| KCl | 285.00 | 2150.00 | 215.00 | 283.00 |
| $KH_2PO_4$ | 83.00 | 830.00 | 83.00 | 13.00 |
| $MgCl_2$ (anhyd.) | — | — | — | — |
| $MgCl_2.6H_2O$ | — | — | — | — |
| $MgSO_4$ (anhyd.) | — | — | — | 74.64 |
| $MgSO_4.7H_2O$ | 152.00 | 1528.00 | 152.00 | — |
| NaCl | 7400.00 | 74000.00 | 5950.00 | 7400.00 |
| $NaHCO_3$ | 1200.00 | — | 1200.00 | — |
| $Na_2HPO_4$ (anhyd.) | — | — | — | 153.70 |
| $Na_2HPO_4.7H_2O$ | 290.00 | 2900.00 | 290.00 | — |
| $ZnSO_4.7H_2O$ | 0.0218 | 0.283 | 0.0283 | — |
| OTHER COMPONENTS: | | | | |
| D-Glucose | 1100.00 | 31000.00 | 1100.00 | 1100.00 |
| HEPES | — | — | 5950.00 | — |
| Hypoxanthine | 4.00 | 40.00 | 4.00 | — |
| Hypoxanthine.Na | — | — | — | 4.68 |
| Linoleic acid | — | — | — | — |
| Lipoic acid | 0.20 | 2.00 | 0.20 | 0.20 |
| Phenol red | 1.20 | 12.00 | 1.20 | 140 |
| Putrescine.2HCl | — | — | — | — |
| Sodium pyruvate | 110.00 | 1100.00 | 110.00 | 110.00 |
| Thymidine | 0.70 | 7.00 | 0.70 | 0.70 |
| AMINO ACIDS: | | | | |
| L-Alanine | 9.00 | 90.00 | 9.00 | 9.00 |
| L-Arginine-HCl | 211.00 | 2110.00 | 211.00 | 211.00 |
| L-Asparagine-$H_2O$ | 15.01 | 150.10 | 15.01 | 33.01 |
| L-Aspartic acid | 13.00 | 1.30.00 | 13.00 | 1.3.00 |
| L-Cysteine | 25.00 | 250.00 | 25.00 | 25.00 |
| L-Cysteine-HCl.$H_2O$ | — | — | — | — |
| L-Glutamic acid | 14.70 | 147.00 | 14.70 | 14.70 |
| L-Glutamine | 146.00 | 1460.00 | 146.00 | 146.00 |
| Glycine | 7.51 | 75.10 | 7.51 | 7.31 |
| L-Histidine-HCl.$H_2O$[b] | 23.00 | 230.00 | 23.00 | 23.00 |
| L-Isoleucine | 2.60 | 26.00 | 2.40 | 2.40 |
| L-Leucine | 13.00 | 130.00 | 13.00 | 13.00 |
| L-Lysine-HCl | 29.00 | 290.00 | 29.00 | 29.00 |
| L-Methionine | 4.43 | 44.80 | 4.48 | 4.48 |
| L-Pheuylalanine | 5.00 | 50.00 | 5.00 | 5.05 |
| L-Proline | 11.50 | 115.00 | 11.50 | 31.50 |
| L-Serine | 10.50 | 105.00 | 10.50 | 10.30 |
| L-Threonine | 3.57 | 35.70 | 3.57 | 3.57 |
| L-Tryptophaa | 0.60 | 6.00 | 0.60 | 0.40 |
| L-Tyrosine | 1.81 | 18.10 | 1.81 | — |
| L-Tyrosine.2Na.$2H_2O$ | — | — | — | 2.68 |
| L-Valine | 3.50 | 35.00 | 3.50 | 3.50 |
| VITAMINS: | | | | |
| Biotia | 0.024 | 0.24 | 0.024 | 0.024 |
| D-Ca pantohenate[e] | 0.715[d] | 7.15 | 0.715 | 0.715[d] |
| Choline chloride | 0.696 | 6.96 | 0696 | 0.696 |
| Folic acid | 1.32 | 13.29 | 1.32 | 1.32 |
| i.Inosinol | 0.341 | 5.41 | 0.541 | 0.541 |
| Niacinamide | 0.615 | 6.15 | 0.615 | 0.615 |
| Pyridine HCl | 0X6 | 2.06 | O.376 | 0.206 |
| Riboflvin | 0.376 | 3.74 | 0.376 | 0.376 |
| Thiamine HCl | 1.00 | 10.00 | 1.00 | .1.00 |
| Vitamin $B_{12}$ | 1.36 | 13.60 | 1.36 | 1.36 |

[1]Ham R.G. (1963) *Exp. Cell. Res, 29*, 515.
[a]Tissue Culture Standards Committee lists this as $CuSO_4.6H_2O$
[b]Original formula lists L-Histidine-HCl at 21.0 mg/L.
[c]Values established by the Tissue Culture Committee.
[d]Varies from Tissue Culture Standards Committee value of 0.236 mg/L.

| F-12 Nutrient Mixture (Ham)[1] | | |
|---|---|---|
| COMPONENT | 320-1765 1X Liquid mg/L | 430-1700 Powder mg/L |
| INORGANIC SALTS: | | |
| $CaCl_2$ (anhyd.) | — | 33.22 |
| $CaCl_2.2H_2O$ | 44.00 | — |
| $CuSO_4.5H_2O$ | 0.0025 | 0.0025 |
| $FeSO_4.7H_2O$ | 0.834 | 0.834 |
| KCl | 223.60 | 223.60 |
| $MgCl_2$ (anhyd.) | — | 57.22 |
| $MgCl_2.6H_2O$ | 122.00 | — |
| NaCl | 7599.00 | 7599.00 |
| $NaHCO_3$ | 1176.00 | — |
| $Na_2HPO_4$ (anhyd.) | — | 142.04 |
| $Na_2HPO_4.7H_2O$ | 268.00 | — |
| $ZnSO_4.7H_2O$ | 0.863 | 0.863 |
| OTHER COMPONENTS: | | |
| D-Glucose | 1802.00 | 1802.00 |
| Hypoxanthine | 4.10 | — |
| Hypoxanthine (sodium salt) | — | 4.77 |
| Linoleic acid | 0.084 | 0.084 |
| Lipoic acid | 0.21 | 0.21 |
| Phenol red | 1.20 | 1.20 |
| Putreacine.2HCl | 0.161 | 0.161 |
| Sodium pyruvate | 110.00 | 110.00 |
| Thymidine | 0.73 | 0.73 |
| AMINO ACIDS: | | |
| L-Alanine | 8.90 | 8.90 |
| L-Arginine.HCl | 211.00 | 211.00 |
| L-Asparagine.$H_2O$ | 15.01 | 15.01 |
| L-Aspartic acid | 13.30 | 13.30 |
| L-Cysteine.HCl.$H_2O$ | 35.12 | 35.12 |
| L-Glutamic acid | 14.70 | 14.70 |
| L-Glutamine | 146.00 | 146.00 |
| Glycine | 7.50 | 7.50 |
| L-Histidine.HCl.$H_2O$ | 20.96 | 20.96 |
| L-Isoleucine | 3.94 | 3.94 |
| L-Leucine | 13.10 | 13.10 |
| L-Lysine.HCl | 36.50 | 36.50 |
| L-Methionine | 4.48 | 4.48 |
| L-Phenylalanine | 4.96 | 4.96 |
| L-Proline | 34.50 | 34.50 |
| L-Serine | 10.50 | 10.50 |
| L-Threonine | 11.90 | 11.90 |
| L-Tryptophan | 2.04 | 2.04 |
| L-Tyrosine | 5.40 | — |
| L-Tyrosine.2Na.$2H_2O$ | — | 7.78 |
| L-Valine | 11.70 | 11.70 |
| VITAMINS: | | |
| Biotin | 0.0073 | 0.0073 |
| D-Ca pantothenate | 0.48 | 0.48 |
| Choline chloride | 13.96 | 13.96 |
| Folic acid | 1.30 | 1.30 |
| i-Inositol | 18.00 | 18.00 |
| Niacinamide | 0.037 | 0.037 |
| Pyridoxine.HCl | 0.062 | 0.062 |
| Riboflavin | 0.038 | 0.038 |
| Thiamine.HCl | 0.34 | 0.34 |
| Vitamin $B_{12}$ | 1.36 | 1.36 |

[1]Ham, R. G. (1965) Proc. Nat. Acad. Sci. 53, 288.

| RPMI Medium 1630[1] | |
|---|---|
| COMPONENT | 328-1855 1X Liquid mg/L |
| INORGANIC SALTs: | |
| Ca(NO$_3$)$_2$.4H$_2$O | 100.00 |
| KCl | 400.00 |
| MgSO$_4$.7H$_2$O | 100.00 |
| NaCl | 6000.00 |
| Na$_2$HPO$_4$.7H$_2$O | 2835.00 |
| OTHER COMPONENTS: | |
| D-Glucose | 2500.00 |
| Glulathione (reduced) | 10.00 |
| Phenol red | 5.00 |
| AMINO ACIDS: | |
| L-Arginine | 200.00 |
| L-Asparagine | 30.00 |
| L-Aspartic acid | 30.00 |
| L-Cystine | 100.00 |
| L-Glutamic acid | 80.00 |
| L-Glutamine | 300.00 |
| Glycine | 15.00 |
| L-Histidine | 35.00 |
| L-Isoleucine | 50.00 |
| L-Leucina | 50.00 |
| L-Lysine HCl | 60.00 |
| L-Methionine | 15.00 |
| L-Phenylalanine | 30.00 |
| L-Proline | 30.00 |
| L-Serine | 50.00 |
| L-Threoaine | 50.00 |
| L-Trypsophan | 10.00 |
| L-Tyrosine | 30.00 |
| L-Valine | 40.00 |
| VITAMINS: | |
| Biota | 0.20 |
| D-Ca pantotbenate | 3.00 |
| Choline chloride | 3.00 |
| Folic acid | 2.00 |
| i-Inositol | 5.00 |
| Niacinamide | 2.50 |
| Para-aminobenzoic acid | 0.50 |
| Pyridoxime-HCl | 2.00 |
| Riboflavin | 0.20 |
| Thiamine-HCl | 5.00 |
| Vitamin B$_{12}$ | 0.05 |

[1]Moore, G.E. and Kitamurs, H. (1968) N.Y. State Journel of Medicine 68, 2034.

| | RPMI Media 1640[1] | | | | | | | | |
|---|---|---|---|---|---|---|---|---|---|
| COMPONENT | 320-1870 1X Liquid mg/L | 320-1875 1X Liquid mg/L | 330-2511 10X Liquid mg/L | 380-2400 1X Liquid mg/L | 430-1800 Powder mg/L | 430-3200 Powder mg/L | 430-3400 Powder mg/L | 320-1838 1X Liquid mg/L | 320-1877 1X Liquid mg/L |
| INORGANIC SALTS: | | | | | | | | | |
| Ca(NO$_3$)$_2$.4H$_2$O | 100.00 | 100.00 | 1000.00 | 100.00 | 100.00 | 100.00 | 100.00 | 100.00 | 100.00 |
| KCl | 400.00 | 400.00 | 4000.00 | 400.00 | 400.00 | 400.00 | 400.00 | 400.00 | 400.00 |
| MgSO$_4$ (anhyd.) | — | — | — | — | 48.84 | 48.84 | 48.84 | — | — |
| MgSO$_4$.7H$_2$O | 100.00 | 100.00 | 1000.00 | 100.00 | — | — | — | 100.00 | 100.00 |
| NaCl | 6000.00 | 6000.00 | 60000.00 | 5300.00 | 6000.00 | 6000.00 | 5850.00 | 6000.00 | 6000.00 |
| NaHCO$_3$ | 2000.00 | 2000.00 | — | 2000.00 | — | — | — | 2000.00 | 2000.00 |
| Na$_2$HPO$_4$ (anhyd.) | — | — | — | — | 800.00 | 800.00 | 800.00 | — | — |
| Na$_2$HPO$_4$.7H$_2$O | 1512.00 | 1512.00 | 15120.00 | 1512.00 | — | — | — | 1512.00 | — |
| OTHER COMPONENTS: | | | | | | | | | |
| D-Glucose | 2000.00 | 2000.00 | 20000.00 | 2000.00 | 2000.00 | 2000.00 | 2000.00 | 2000.00 | 2000.00 |
| Glutathione (reduced) | 1.00 | 1.00 | 10.00 | 1.00 | 1.00 | 1.00 | 1.00 | 1.00 | 1.00 |
| HEPES | — | — | — | 5958.00 | — | — | 5957.50 | — | — |
| Phenol red | 5.00 | 5.00 | 50.00 | 5.00 | 5.00 | — | 5.00 | — | 5.00 |
| AMINO ACIDS: | | | | | | | | | |
| L-Arginine | 200.00 | 200.00 | 2000.00 | 200.00 | 200.00 | 200.00 | 200.00 | 200.00 | 200.00 |
| L-Asparagine | 50.00 | 50.00 | 500.00 | 50.00 | 50.00 | 50.00 | 50.00 | 50.00 | 50.00 |
| L-Aspartic acid | 20.00 | 20.00 | 200.00 | 20.00 | 20.00 | 20.00 | 20.00 | 20.00 | 20.00 |

-continued

RPMI Media 1640[1]

| COMPONENT | 320-1870 1X Liquid mg/L | 320-1875 1X Liquid mg/L | 330-2511 10X Liquid mg/L | 380-2400 1X Liquid mg/L | 430-1800 Powder mg/L | 430-3200 Powder mg/L | 430-3400 Powder mg/L | 320-1838 1X Liquid mg/L | 320-1877 1X Liquid mg/L |
|---|---|---|---|---|---|---|---|---|---|
| L-Cystine | 50.00 | 50.00 | 500.00 | 50.00 | — | — | — | 50.00 | 50.00 |
| L-Cystine.2HCl | — | — | — | — | 65.15 | 65.15 | 65.15 | — | — |
| L-Glutamic acid | 20.00 | 20.00 | 200.00 | 20.00 | 20.00 | 20.00 | 20.00 | 20.00 | 20.00 |
| L-Glutamine | — | 300.00 | 3000.00 | 300.00 | 300.00 | 300.00 | 300.00 | 300.00 | 300.00 |
| Glycine | 10.00 | 10.00 | 100.00 | 10.00 | 10.00 | 10.00 | 10.00 | 10.00 | 10.00 |
| L-Histidine | 15.00 | 15.00 | 150.00 | 15.00 | 15.00 | 15.00 | 15.00 | 15.00 | 15.00 |
| L-Hydroxproline | 20.00 | 20.00 | 200.00 | 20.00 | 20.00 | 20.00 | 20.00 | 20.00 | 20.00 |
| L-Isoleucine | 50.00 | 50.00 | 500.00 | 50.00 | 50.00 | 50.00 | 50.00 | 50.00 | 50.00 |
| L-Leucine | 50.00 | 50.00 | 500.00 | 50.00 | 50.00 | 50.00 | 50.00 | 50.00 | 50.00 |
| L-Lysine.HCl | 40.00 | 40.00 | 400.00 | 40.00 | 40.00 | 40.00 | 40.00 | 40.00 | 40.00 |
| L-Methionine | 15.00 | 15.00 | 150.00 | 15.00 | 15.00 | 15.00 | 15.00 | 15.00 | 15.00 |
| L-Phenylaline | 15.00 | 15.00 | 150.00 | 15.00 | 15.00 | 15.00 | 15.00 | 15.00 | 15.00 |
| L-Proline | 20.00 | 20.00 | 200.00 | 20.00 | 20.00 | 20.00 | 20.00 | 20.00 | 20.00 |
| L-Serine | 30.00 | 30.00 | 300.00 | 30.00 | 30.00 | 30.00 | 30.00 | 30.00 | 30.00 |
| L-Threonine | 20.00 | 20.00 | 200.00 | 20.00 | 20.00 | 20.00 | 20.00 | 20.00 | 20.00 |
| L-Tryptophan | 5.00 | 5.00 | 50.00 | 5.00 | 5.00 | 5.00 | 5.00 | 5.00 | 5.00 |
| L-Tyrosine | 20.00 | 20.00 | 200.00 | 20.00 | — | — | — | 20.00 | 20.00 |
| L-Tyrosine.2Na.2H$_2$O | — | — | — | — | 28.83 | 28.83 | 28.83 | — | — |
| L-Valine | 20.00 | 20.00 | 200.00 | 20.00 | 20.00 | 20.00 | 20.00 | 20.00 | 20.00 |
| VITAMINS: | | | | | | | | | |
| Biotin | 0.20 | 0.20 | 2.00 | 0.20 | 0.20 | 0.20 | 0.20 | 0.20 | 0.20 |
| D-Ca pantothenate | 0.25 | 0.25 | 2.50 | 0.25 | 0.25 | 0.25 | 0.25 | 0.25 | 0.25 |
| Choline chloride | 3.00 | 3.00 | 30.00 | 3.00 | 3.00 | 3.00 | 3.00 | 3.00 | 3.00 |
| Folic acid | 1.00 | 1.00 | 10.00 | 1.00 | 1.00 | 1.00 | 1.00 | 1.00 | 1.00 |
| i-Inositol | 35.00 | 35.00 | 350.00 | 35.00 | 35.00 | 35.00 | 35.00 | 35.00 | 35.00 |
| Niacinamide | 1.00 | 1.00 | 10.00 | 1.00 | 1.00 | 1.00 | 1.00 | 1.00 | 1.00 |
| Para-aminobenzoid acid | 1.00 | 1.00 | 10.00 | 1.00 | 1.00 | 1.00 | 1.00 | 1.00 | 1.00 |
| Pyridoxine-HCl | 1.00 | 1.00 | 10.00 | 1.00 | 1.00 | 1.00 | 1.00 | 1.00 | 1.00 |
| Riboflavin | 0.20 | 0.20 | 2.00 | 0.20 | 0.20 | 0.20 | 0.20 | 0.20 | 0.20 |
| Thiamine.HCl | 1.00 | 1.00 | 10.00 | 1.00 | 1.00 | 1.00 | 1.00 | 1.00 | 1.00 |
| Vitamin B$_{12}$ | 0.005 | 0.005 | 0.05 | 0.005 | 0.005 | 0.005 | 0.005 | 0.005 | 0.005 |

[1]Moore, G. E., Gerner, R. E., and Franklin, H. A. (1967) J.A.M.A. 199, 519.

The serum component may be present in the culture in an amount of at least 1% (v/v) to 50% (v/v). The preferred range will depend on whether or not serum is being used alone or is, at least in part, replaced by a serum replacement. When using no serum replacement, the serum concentration may be preferably in the neighborhood of 10 to 30% (v/v). The third component, corticosteriod, may be present in an amount of from $10^{-6}$M to $10^{-4}$ M, and is preferably present in an amount of from $5 \times 10^{-6}$ to $5 \times 10^{-5}$ M. Alternatively, the serum component can be replaced by any of several standard serum replacement mixtures which typically include insulin, albumin, and transferrin, lecithin, selenium or cholesterol. See, *Migliaccio et al, Exp. Hematol.* (1990) 18:1049–1055, *Iscove et al, Exp. Cell Res.* (1980) 126:121–126, and *Dainiak et al, J. Clin. Invest.* (1985) 76:1237–1242.

In addition to supporting the proliferation of human hematopoietic stem cells, the applications of these same conditions leads to the controlled production or depletion of specific lineage of blood cells. The inventors have discovered that when IL-3 and Epo, with or without GM-CSF, are used as described above one obtains lineage specific development of red blood cells. The inventors have also observed that T and B lymphocytes are lost from these cultures, during the same period of time in which the myeloid progenitor and cell mass is increasing. The inventors have also observed that leukemic cells are lost from these cultures over time.

The inventors also observed that with the cultures of the invention T and B lymphocytes are lost over time. As noted above, there are several T-cell-derived diseases and therapeutic concerns. For example, the autoimmune deficiency diseases (e.g., AIDS) result because of abnormal T-cell function caused by direct viral infection. Since this order results as a direct infection of the mature T-cell, and is not derived from defective hematopoietic stem or progenitor cells selective eradication of the mature T-cells has notable potential therapeutic benefit.

T-cell depletion has other applications as well. A limiting factor to the improved success of allogeneic bone marrow transplant is T-cell mediated. Depletion of T-cells from a stem/progenitor cell population prior to allogeneic transplant would enhance the reingraftment success by reducing the T-cell mediated graft versus host-rejection response.

The inventors have discovered that the present methods, including the present culture media conditions, which allow for the in vitro replication and differentiation of human stem and hematopoietic progenitor cells do not allow for maintenance of all hematopoietic cell classes. Although in the present methods and composition, human stem and hematopoietic progenitor cells are capable of in vitro replication and differentiation, human T-cells and B-cells, a major class of peripheral blood cells, do not proliferate or maintain viability in these in vitro culture conditions.

More particularly, T-cells require, among other factors, the growth factor interleukin-2 (IL-2) to remain viable. T-cells grown without such proper support die in approximately 3 to 4 days in a medium substantially free of IL-2. As a result, over a period of time when the viability and proliferative capacity of human stem and hematopoietic progenitor cells are maintained in accordance with the invention, the human T-cells contained in the human hematopoietic mononuclear cell population die, if the medium is substantially free of IL-2.

In accordance with this embodiment of the invention, a mixed human hematopoietic mononuclear cell fraction can be effectively depleted of T-cells and B-cells, under conditions which allow for expansion of stem and progenitor cells.

This method of selective T-cell depletion of human hematopoietic cell populations has notable therapeutic value as noted above. These include the following two applications:

1. Supportive treatment alone, or when used as adjuvant therapy, for curative treatment of AIDS and related T-cell diseases resulting from the dysfunction of the mature T-cell because of viral infection or other T-cell-specific functional disruption. The present culture conditions can be used to deplete disease-causing T-cells, while allowing for the survival, with or without their expansion, of human hematopoietic stem and/or progenitor cells. The T-cell-depleted hematopoietic cell population can then be used for reingraftment of patient bone marrow. The reestablished marrow will then produce anew, normal T-cell population. In its application to AIDS therapy, this procedure itself would not serve to necessarily eradicate the HIV from the patient, and reinfection of the newly developed T-cell in vivo is likely. Accordingly, this therapy would be considered as supportive, but, if used with other virus-eradication procedures, this procedure is operative for curative treatment protocols as well.

2. Allogeneic bone marrow transplant whereby a human hemotopoietic stem/progenitor cell population is depleted of viable T-cells and then used to reestablish the hematopoietic system in a recipient individual. The depletion of the T-cell population will increase the prospect of successful reingraftment by decreasing the graft versus host rejection process.

The present method of T-cell and B-cell depletion should be contrasted with methods for isolating and purifying progenitor cells (see, e.g., U.S. Pat. No. 5,061,620 as representative). The reported methods do not provide a method for the long term culture of viable and replicating stem cells, while the present method affords just such a result.

It should be understood that the present method for controlling the lineage development in a human hematopoietic tissue system may be practiced in conjunction with genetic transformation of at least a portion of the stem cells in the hematopoietic tissue system.

In another embodiment, the present invention provides a method for assaying the effect of a substance or substances and/or physical condition on a hematopoietic cell culture or the process of hematopoiesis. In accordance with this embodiment, one may add to a cell culture, carried out in accordance with the invention, at least one substance suspected of having an affect, which may be either beneficial or detrimental, on the cell culture. One may then compare the cell culture state obtained in the absence of the substance being tested to the cell culture state obtained in the presence of the substance.

Compounds or substances which may be tested include those which are expected to exert some effect on the hematopoietic system. Such compounds include, for example, hematopoietic growth factors, drugs, hormones, etc.

It should be understood that the present assay also permits the determination of the effect of substances endogenously produced by the present hematopoietic system. The effect of an endogenously produced substance may be assayed by adding to the medium a compound which either reduces the effective concentration of the endogenously produced substance and/or inhibits the action of the endogenously produced substance. Examples of such compounds include monoclonal antibodies, which bind to and neutralize endogenously produced growth factors, and antagonists, which bind to and block growth factor receptors on the surface of cells.

The present assay may also be used to ascertain the effect of physical conditions on the hematopoietic system or hematopoietic process. Such conditions include, for example, temperature, pressure, light intensity, gravity, etc. The effect of temperature, pressure, and light intensity may be determined by varying these parameters using conventional techniques and apparatus, such as heaters, refrigerators, pressurized or reduced-pressure chambers, and light sources. The effect of gravity may be determined by, e.g., carrying out the present culture in a zero-gravity environment, such as the space shuttle. The present assay may also be used to determine the effect of the particular configuration of the cell culture chamber, such as the nature of the surface which supports the adherent cell population.

Of course, it should be understood that the present assay is not limited to determining the effect of a single chemical substance or physical condition but may be used to detect the effect of the combined action of any number of chemical substances and/or physical conditions.

The parameters which can be monitored in carrying out the present assay include the cell population profile of the hematopoietic cell culture, the total cell population, the relative population of any particular type of cell, the presence, absence, or concentration of any other substance in the medium being removed from the culture, the consumption of nutrients, the morphology of any or all of the particular cell types present in the culture, the lifetime and duration of the culture, and the kinetics of hematopoiesis.

Thus, the present invention provides a functioning in vitro human hematopoietic tissue system which may serve as a model for the study of the naturally occurring in vivo hematopoietic system and the process of hematopoiesis. Accordingly, the effect of any chemical substance and/or physical condition on the hematopoietic system or the process of hematopoiesis may be determined by the present assay. It should be recognized that the present assay exhibits a significant advantage in that the effects of (i) slow acting substances and/or conditions or (ii) substances and/or conditions for which the effect exhibits a lag phase may be readily determined, because the present system provide a long term functioning hematopoietic tissue system.

It should also be understood that the present assay may be carried out when at least a portion of the stem cells in the human hematopoietic tissue system have been genetically transformed. Such genetic transformation may be used to introduce genetic markers useful for the subsequent identification of cells derived from the transformed stem cells. In addition, such genetic transformation may also serve as a method for introducing into the medium the chemical substance to be studied. Thus, when stem cells are transformed with a gene encoding for a particular substance and the appropriate regulatory sequences, the production of the substance by either the stem cell or a cell derived therefrom will provide a constant source of the substance.

In another embodiment, the present invention provides an improved method of bone marrow transplantation. Thus, by culturing bone marrow tissue according to the present method may of the drawbacks attendant to conventional bone marrow transplants may be avoided.

Thus, as noted above, the present method of bone marrow transplantation may be advantageously applied in situations in which the bone marrow tissue has been previously removed from a patient, before the patient is subjected to either chemotherapy or radiation therapy for the treatment of cancer, and is then implanted in the same patient after completion of the session of therapy. Since the present methods permit the expansion of the hematopoietic culture, a smaller quantity of tissue may removed form the patient prior to therapy. In addition, since culture of the bone marrow tissue according to the present method results in the depletion and extinction of malignant cells, implantation of the tissue cultured according to the present method poses a reduced risk of reintroducing malignant cells which may have metastasized into the bone marrow.

In the setting of allogeneic bone marrow transplants, the present method also exhibits distinct advantages. Thus, because culturing according to the present method, using medium substantially free of IL-2, results in a bone marrow culture substantially free of T-cells and B-cells and since such cells are principally involved in graft versus host disease, implantation of allogeneic bone marrow tissue cultured according to the present method poses a reduced risk of graft versus host disease.

It should be stressed that these advantages are uniquely afforded by the present invention. Thus, it is the ability of the present culture techniques to maintain and/or expand a viable and functioning in vitro hematopoietic tissue system for a time sufficient to effect the depletion of malignant cells and/or T-cells and B-cells that enables the implantation of bone marrow tissue substantially free of malignant cells and/or T-cells and B-cells. Culturing bone marrow tissue, for a time sufficient to effect such depletions, by conventional techniques would not result in a functioning in vitro hematopoietic tissue system containing viable stem cells.

The present method of bone marrow transplantation may be carried out as follows: removing a tissue sample from a donor; culturing said tissue sample according to the present method; and implanting said cultured tissue in a donee. As noted above the donor and donee may be the same or different.

The tissue sample may be obtained from the donor according to conventional methods using conventional apparatus. Apparatus for and methods of bone marrow transplantation are disclosed in U.S. Pat. Nos. 4,481,946 and 4,486,188, which are incorporated herein by reference.

After the tissue sample has been obtained, it is then cultured according to the present method, for a time sufficient to achieve the desired expansion and/or cell depletion. The cultured tissue may then be implanted in the donee, again, according to conventional techniques.

It should be understood that the present method of bone marrow transplantation may be used advantageously in conjunction with genetic transformation of at least a portion of the stem cells in the tissue to be implanted in the donee. The advantages of stem cell transformation in gene therapy are discussed above. Thus, the present method of bone marrow transplantation, when used in conjunction with genetic transformation of stem cells in the implanted tissue, represents an improved method of gene therapy.

Having generally described this invention, a further understanding can be obtained by reference to certain specific examples which are provided herein for purposes of illustration only and are not intended to be limiting unless otherwise specified.

EXAMPLES

Example 1: Medium Replacement

Materials and Methods

Cells: Human bone marrow cells were obtained from heparinized aspirates from the iliac crest of informed and consenting individuals. The bone marrow was separated by a Ficoll-Paque (Pharmacia, No. 17-0840-02) density gradient centrifugation and the low density cells ($<1.077$ gm/cm$^3$) were collected and washed 3 times with Iscove's Modified Dulbecco's Medium (IMDM). The cells were counted between the second and third washes. The cells were then seeded onto 24-well tissue culture plates (Costar No. 3524) in duplicate or triplicate at 1, 2, and $5 \cdot 10^6$ cells/ml at 322 $\mu$l/well.

Long-term culture conditions: The low density cells were incubated in IMDM supplemented with 10% fetal calf serum (Hyclone Laboratories), 10% horse serum (Hyclone Laboratories), 1% penicillin/streptomycin (Sigma, 10,000 U/ml penicillin G and 10 mg/ml streptomycin, Cat. No. P3539), and $10^{-5}$ M hydrocortisone (17-Hydroxycorticosterone, Sigma, Cat. No. H0888) in a humidified 5% $CO_2$/95% air atmosphere. The cultures were treated with one of three medium exchange schedules, 100% daily medium exchange (7/wk), 50% daily medium exchange (3.5/wk), or 50% biweekly medium exchange (1/wk). Twice per week during the medium exchange, 50% of the non-adherent cells were removed from each culture well and counted using a hemocytometer. When the cells were removed for counting (twice/week), all of the medium removed during feeding of the 3.5/wk and 1/wk cultures was saved for cell counts and fresh medium returned to the wells. The 7/wk cultures required saving ½ of the removed medium for cell counts, while centrifuging and returning the non-adherent cells in the remaining ½ of the medium removed. Fresh medium was then added to each well to replace the medium removed for cell counts. On days when the cells were not removed for counting, 100% or 50% of the medium was removed from each of the 7/wk and 3.5/wk culture wells respectively, the cells were centrifuged and returned to the original wells with additional fresh medium.

Methycellulose and morphologic assays: Once every other week, the non-adherent cells removed for cell counts were plated in methylcellulose in the presence of erythropoietien, GM-CSF, and IL-3, and the Granulocyte Macrophage-Colony Forming Units (CFU-GM) were enumerated. Aliquots of removed cells were cytocentrifuged, stained with Wright-Giemsa, and differential cell counts were performed.

Statistical analysis: The biweekly cell production results are expressed as the means ±SEM from replicate cultures. The probability of significant differences between groups of cultures was determined by comparing the normalized cumulative cell production values from the rapidly exchanged cultures (7/wk and 3.5/wk) to the matched control cultures (1/wk) using a paired t-test. Statistical significance was taken at the 5% level.

Results

Kinetics of nonadherent cell production: Nonadherent cell production was examined both as a function of inoculum cell density (over the range $1-5 \cdot 10^6$ cells/ml) and medium exchange rate. The medium exchange rate was varied from one medium volume exchange per week, the traditional Dexter culture rate, to seven medium volume exchanges per week. The biweekly number of cells collected was normalized by dividing by the number of cells inoculated per culture. At each medium exchange rate, the normalized cell collection curves did not change significantly with inoculum density. The cell production for the cultures maintained at the three medium perfusion rates of 7/wk, 3.5/wk and 1/wk were similar when normalized to the number of cells inoculated per culture. Comparison of the final cumulative cell productions between inoculum densities showed no significant differences, at any of the three medium exchange rates (p>.20 by a paired t-test for all pairs of samples).

The medium exchange rate, in contrast, strongly influenced the rate and longevity of cell production in these cultures. Cell production of the cultures exchanged at 1/wk (control), 3.5/wk, and 7/wk all decayed over the first few weeks. Differences in culture productivity, however, became apparent after week 3 in culture. Between weeks 3 to 10, the cell production was constant in the 7/wk cultures, constant at a lower level in the 1/wk cultures, but increased exponentially in the 3.5/wk cultures. After weeks 10 to 12, cell production declined in all cultures until culture termination. Results for the 1/wk exchanged cultures are equivalent to those commonly observed in traditional human Dexter cultures in a variety of systems, whereas the rapidly exchanged cultures of 3.5 and 7/wk showed increased cell productivity when compared to previous optimum culture methods. Cultures in which ½ of the medium was exchanged daily (3.5/wk) maintained increased cell production for substantially longer than either the control (1/wk) or complete daily exchange (7/wk) cultures. Between weeks 3 and 9, the number of nonadherent cells collected from the 3.5/wk exchanged cultures increased exponentially with a doubling every 2.1 weeks.

The cell production under the 3.5/wk and 1/wk protocols can be directly compared by plotting the cell production under the 3.5/wk exchange rate as a percentage of the production of the cultures with an exchange rate of 1/wk. This comparison shows that during the initial decay phase the cell production under the two protocols is similar. However, between weeks 3.5 and 18, the cell production under the 3.5/wk exchange rate is consistently higher.

The proliferative potential of the cultures can be measured by their ability to produce cells following the initial decay. The normalized cumulative cell production following week 3 was independent of the cell inoculation density for the medium exchange rates of 7/wk, 3.5/wk. Cell production data from the cultures at similar medium exchange rates were qualitatively and statistically similar, and were therefore density averaged and combined to obtain a larger statistical sample. The density averaged cumulative cell production between weeks 3.5 and 20 was: 0.22 for the 7/wk; 0.40 for the 3.5/wk; and 0.15 for the 1/wk cultures. The increase in the medium exchange rate from 1/wk to 7/wk thus increased the cell production about 60% over the typical Dexter culture medium exchange schedule. The 3.5/wk exchange rate resulted in almost 3-fold cumulative cell production increase compared to the 1/wk Dexter protocol. Statistical analysis of these data using a paired t-test, demonstrated significant differences between both the 7/wk vs. 1/wk and the 3.5/wk vs. 1/wk at the 5% level of significance. The medium exchange rate of 3.5/wk thus improves the cell production rate over the traditional Dexter protocol of 1/wk.

Granulocyte-macrophage progenitor cell production: Granulocyte-macrophage progenitor cell assays were performed from replicates of a given medium perfusion schedule and inoculum density (Table 1). The medium perfusion rate had a pronounced effect on the number of granulocyte-macrophage progenitor cells produced. The 3.5/wk medium exchange cultures showed the greatest longevity in terms of progenitor cell production. These cultures produced progenitors at a stable rate between weeks 4 and 18. The optimum conditions in terms of progenitor cell production are the cultures exchanged 3.5 times per week and inoculated at $5 \cdot 10^6$ cells/ml. These cultures produced a significant number of progenitor cells until week 20. Statistical analysis, using a paired t-test, showed that the optimum medium exchange rate cultures of 3.5/wk produced significantly more granulocyte-macrophage progenitor cells after week 8 than did the corresponding 7/wk and 1/wk cultures at all three inoculation densities at the 1% level of significance. The number of progenitor cells produced is important as it is an indirect measure of stem cell renewal. Progenitor cells can only be present after several weeks in culture by differentiation from an earlier cell, presumably a stem cell, which is still present in culture. Thus, these data suggest that more physiologic, rapid medium/serum exchange rate and higher cell densities may have provided conditions that supported some degree of stem cell renewal for five months.

Nonadherent cell morphology: To determine whether the prolonged hematopoiesis supported by the 3.5/wk cultures was qualitatively different from the other cultures, the nonadherent cells collected between weeks 10 and 19 were stained and typed morphologically. At the exchange rates of 1/wk and 7/wk, the cells produced were mostly macrophages by week 15 and thereafter (Table 2), which is similar to results from studies in other laboratories. In contrast, the cultures perfused at a rate of 3.5 medium volumes per week and seeded at $5 \cdot 10^6$ cells/ml produced granulocytes as well as macrophages through week 19.

Thus, rapid medium exchange effectively resulted in the selective production of granulocytes throughout the cultures, a feature which was not present without the application of rapid medium exchange or perfusion. This result supports the hypothesis that standard long term human hematopoietic culture conditions are suboptimal, and that proper in vitro culture of hematopoietic cells under the presently described conditions allows the production of blood cells of diverse lineages.

TABLE 1

The average number of nonadherent progenitor cells removed from long term bone marrow cultures (LTBMCs) as a function of the medium perfusion rate and inoculum density.

| Week | 7/wk | | | 3.5/wk | | | 1/wk | | |
| | $5 \times 10^6$ per ml | $2 \times 10^6$ per ml | $1 \times 10^6$ per ml | $5 \times 10^6$ per ml | $2 \times 10^6$ per ml | $1 \times 10^6$ per ml | $5 \times 10^6$ per ml | $2 \times 10^6$ per ml | $1 \times 10^6$ per ml |
|---|---|---|---|---|---|---|---|---|---|
| 2 | 237 ± 27 | 11 ± 3.3 | 106 ± 5 | 120 ± 16 | 132 ± 7.9 | 167 ± 13 | 368 ± 29 | 94 ± 20.8 | 335 ± 46 |
| 4 | 149 ± 21 | 101 ± 5.1 | 104 ± 10 | 93 ± 10 | 37 ± 5.6 | 20 ± 0 | 21 ± 1.3 | 2 ± 0 | 8 ± 4.4 |
| 6 | 47.7 ± 7 | 12 ± 2.5 | 8 ± 0 | 17 ± 3 | 6 ± 4.1 | 5 ± 2.7 | 13 ± 5.1 | 1 ± 0 | 1 ± 0 |

TABLE 1-continued

The average number of nonadherent progenitor cells removed from long term bone marrow cultures (LTBMCs) as a function of the medium perfusion rate and inoculum density.

| | 7/wk | | | 3.5/wk | | | 1/wk | | |
|---|---|---|---|---|---|---|---|---|---|
| Week | $5 \times 10^6$ per ml | $2 \times 10^6$ per ml | $1 \times 10^6$ per ml | $5 \times 10^6$ per ml | $2 \times 10^6$ per ml | $1 \times 10^6$ per ml | $5 \times 10^6$ per ml | $2 \times 10^6$ per ml | $1 \times 10^6$ per ml |
| 8 | 40 ± 3 | 0 | 4 ± 0 | 38 ± 6 | 24 ± 2.7 | 10 ± 3 | 34 ± 7.4 | 0 | 0 |
| 10 | 0 | 0 | 0 | 28 ± 8.3 | 10 ± 2.9 | 5 ± 1.3 | 8 ± 2.3 | 2 ± 2.3 | 0 |
| 12.5 | 0 | 6 ± 2.3 | 0 | 8 ± 2.3 | 0 | 0 | 0 | 0 | 0 |
| 14 | 0 | 0 | 0 | 22 ± 6.4 | 6 ± 1.3 | 2.5 ± 1.2 | 3 ± 1.3 | 0 | 0 |
| 16 | 6 ± 2.2 | 0 | 0 | 24 ± 7.6 | 4 ± 1.7 | 2 ± 1.3 | 9 ± 3.6 | 0 | 0 |
| 18 | 0 | 0 | 0 | 24 ± 6.3 | 4 ± 1.3 | 0 | 0 | 0 | 0 |
| 20 | 0 | 0 | 0 | 5 ± 0 | 4 ± 0 | 3 ± 0 | 1 ± 0 | 0 | 0 |
| 22 | 2 ± 1.3 | 0 | 0 | 4 ± 1.3 | 10 ± 3 | 0 | 0 | 0 | 0 |
| 10–22* | 8 ± 3.5 | 6 ± 2.3 | 0 | 115 ± 32.2 | 40 ± 11.2 | 12.5 ± 3.8 | 21 ± 7.2 | 2 ± 7 | 0 |

Replicate samples at each medium perfusion rate and inoculum density were pooled and are each tabulated as one mean ± SEM.
*Cumulative CFU-GM production after week 8 is statistically greater in the 3.5/wk cultures than the corresponding cultures perfused at 7/wk or 1/wk at all inoculum densities at the 1% level of significance.

Physical appearance: The medium exchange rate significantly affected the physical appearance of the cultures. By 10 weeks in culture, the 7/wk cultures had large number of adipose cells in the stroma while the 3.5/wk cultures had few fat cells and the 1/wk cultures never developed fat cells. At culture termination at 26 weeks, the stroma of the 7/wk cultures were composed of approximately 20–30% fat cells while the 3.5/wk cultures still only had a few fat cells. Adherent colony distribution also varied between cultures with different medium perfusion rate. Adherent colonies in the 3.5/wk cultures persisted longer than those in the 7/wk and 1/wk cultures.

density gradient centrifugation and the low density cells (<1.077 gm/cm$^3$) were collected and washed 3 times with IMDM. The cells were counted between the second and third washes. The cells were then seeded onto 6-well tissue culture plates (Costar No. 3406) or collagen coated 6-well plates (rat tail type 1 collagen, Biocoat. Collaborative Research Inc. Cat. No. 40400) in duplicate 5·10$^6$ cells/ml at 1.5 ml/well.

Culture medium: The medium used was IMDM (Gibco Laboratories. Cat. No. 430-2200) containing 10% fetal calf serum (Hyclone Laboratories), 10% horse serum (Hyclone Lab-oratories), 1% penicillin/streptomycin (Sigma, 10,000

TABLE 2

Nonadherent cell morphology as a function of the medium perfusion rate and inoculum density.

| Medium perfusion rate | weeks | $5 \times 10^8$ per ml | | | $2 \times 10^8$ per ml | | | $1 \times 10^8$ per ml | | |
|---|---|---|---|---|---|---|---|---|---|---|
| | | % Mø | % G | % myeloid precursors | % Mø | % G | % myeloid precursors | % Mø | % G | % myeloid precursors |
| 7/wk | 10.4 | 25 | 57 | 18 | 57 | 32 | 11 | 52 | 34 | 14 |
| | 13.4 | 49 | 34 | 17 | 92 | 5 | 3 | 63 | 22 | 15 |
| | 15.4 | 66 | 19 | 16 | 79 | 19 | 2 | 54 | 7 | 29 |
| | 19 | 93 | 5 | 1 | 96 | 3 | 1 | 100 | 0 | 0 |
| 3.5/wk | 10.4 | 50 | 27 | 23 | 45 | 38 | 17 | 39 | 45 | 17 |
| | 13.4 | 23 | 59 | 19 | 27 | 56 | 17 | 36 | 47 | 17 |
| | 15.4 | 41 | 38 | 21 | 44 | 27 | 29 | 67 | 13 | 21 |
| | 19 | 58 | 37 | 5 | 88 | 9 | 3 | 99 | 1 | 0 |
| 1/wk | 10.4 | 59 | 21 | 20 | 60 | 11 | 29 | ND | ND | ND |
| | 13.4 | 56 | 25 | 20 | 19 | 36 | 46 | 43 | 7 | 50 |
| | 15.4 | 76 | 4 | 20 | ND | ND | ND | 46 | 39 | 15 |
| | 19 | 100 | 0 | 0 | 100 | 0 | 0 | 100 | 0 | 0 |

Data are for pooled replicate samples at each medium perfusion rate and inoculum density and are shown as the percentage of macrophages (% Mø), granulocytes (mature granulocytes and bands, % G), and immature granulocytes precursors (metamyelocytes, myelocytes, promyelocytes and blasts).

Example 2

Medium Replacement Combined with Supplementation of Medium with Hemotopoietic Growth Factors Materials and Methods Cells: Human bone marrow cells were obtained following informed consent from heparinized aspirates of the iliac crest bone marrow, under a protocol approved by the University of Michigan Human Investigation Committee. The bone marrow was separated by a Ficoll-Paque (Pharmacia)

U/ml penicillin G and 10 mg/ml streptomycin, Cat. No. P3539), and $10^{-5}$M hydrocortisone (17-Hydroxycorticosterone, Sigma, Cat. No. H0888).

Hematopoietic growth factors (HGH): Due to the frequent culture supplementation via rapid medium exchange, hematopoietic growth factors were added daily to the medium at approximately 1/20 of the concentrations found to promote maximal colony formation in clonal assays. The concentrations used were 1 ng/ml of IL-3, 1 ng/ml of GM-CSF (Amgen Biologicals, Cat. No. 13050), 0.1 U/ml of Epo (Terry Fox Labs. Vancouver, Canada). In this and all of the following examples, a unit of activity for any given component is as defined by the supplier listed.

Hematopoietic progenitor cell assay: Nonadherent hematopoietic cells removed from culture were counted and plated at $1 \cdot 10^5$ cells/ml or fewer cells in methylcellulose. GM-CSF and Epo were added to the methylcellulose at 20 ng/ml and 2 U/ml, respectively. The cells were plated in 24 well plates at 0.25 ml/well and incubated at 37° C. for 14 days. The colonies were then counted under an inverted microscope and colonies greater than 50 cells were scored as GM-colony forming units (CFU-GM), erythroid burst-forming unit (BFU-E), or granulocyte erythroid megakaryocyte macrophage-colony forming unit (CFU-GEMM).

LTBMC conditions: The cultures were incubated at 37° C. in a humidified 5% $CO_2$/95% air atmosphere and perfused (medium exchanged) at a rate of 50% daily medium exchange. During the first week in culture, all cells removed during the daily medium exchange were centrifuged and returned to the original wells. After the first week in culture, 50% of the total nonadherent cells were removed from the cultures on a biweekly basis during the medium exchange, mononucleated cells counted, and fresh medium returned to the wells. The remaining five days per week when the cells were not counted, 50% of the medium was removed from each of the culture wells and replaced with fresh medium, the removed medium was centrifuged, the medium decanted from the cell pellet, and the cells returned to their original wells.

Statistical analysis: The probability of significant differences between groups of cultures was determined by comparing the normalized cumulative cell production values from the rapidly perfused cultures supplemented with hematopoietic growth factors to the matched untreated control cultures using a paired t-test. Statistical significance was taken at the 5% level. There were no statistical differences between matched rapidly perfused LTBMCs cultured on tissue culture plastic and type I rat tail collagen at the 5% level. Therefore, the data for the plastic and collagen matrix were combined for presentation in this and all other figures and statistical analysis performed on the combined data.

Results:

Kinetics of cell production in rapidly exchanged growth factor supplemented LTBMCs: As a first test of the hypothesis that the longevity and production of specific lineages of mature cells can be influenced by supplementation of HGFs, we established rapidly exchanged in vitro bone marrow cultures that were supplemented with IL-3 or Epo. In these cultures, 50% of the medium was removed daily and replaced with an equal volume of fresh medium supplemented with IL-3 or Epo. The cells removed were then centrifuged, the medium decanted and discarded, the cells resuspended, and the cells returned to the original cultures. IL-3 and Epo individually enhanced the cell productivity of rapidly exchanged LTBMCs. The cultures containing Epo alone initially had a high cell production rate due to substantial terminal erythroid differentiation. However, by week four erythropoiesis had ceased and the cell production rate had decreased to the level of the control cultures. IL-3 and Epo induced an average increase in nonadherent cell production over controls throughout the 18 weeks of culture of 175% and 173%, respectively.

Next, combinations of growth factors proved to be more effective in increasing the nonadherent cell production rate and the diversity of lineages of cells produced. The highest rate of cell production was observed for the combination of IL-3+GM-CSF+Epo. These cultures produced approximately 25% of the number of cells inoculated biweekly during the first 6 weeks in culture and had an average 4.8-fold increase in nonadherent cell production over controls during weeks 2–8. The combination of IL-3+GM-CSF produced an average 3.5-fold increase in nonadherent cells as compared to controls through week 8. In separate experiments, adding neither IL-6 nor G-CSF to the combination of IL-3+GM-CSF+Epo improved the nonadherent cell production rate, but instead resulted in cell production rates indistinguishable from the cultures containing the combination of IL-3+GM-CSF. In all cases, the stimulatory effect on cell production induced by the addition of HGFs was maximal between weeks 0 to 8, although cell production was higher than the controls throughout the culture.

The combinations of HGFs lead to high absolute numbers of nonadherent cells produced in rapidly exchanged LTBMCS. The productivity of the cultures can be shown by comparing the cumulative number of cells produced over time ($\Sigma_{i=1}^{n} C_i$, $C_i$ being the number of nonadherent cells collected at time i), relative to the number of cells inoculated ($C_o$) by plotting the ratio ($\Sigma_{i=1}^{n} C_i/C_o$) as a function of time. When this ratio exceeds unity, a culture has produced more cells than were inoculated and the culture has led to an expansion in cell number.

The combination of IL-3+GM-CSF+Epo induced cumulative cell production that was more than 3-fold greater than the number of cells inoculated. The cell production rate was the highest during the first 6 weeks in culture during which time the culture produced approximately as many cells as were inoculated every two weeks. This maximum cell production rate was 15% of the estimated in vivo bone marrow cell production rate where 50% of the myeloid cell mass is generated daily. The combination of IL-3+GM-CSF resulted in more than a 2-fold expansion in cell number and at rates comparable to the combination of IL3+GM-CSF+Epo during weeks 3–7 in culture. Untreated rapidly exchanged (50% daily medium exchange) and slowly exchanged (50% medium exchange biweekly) control cultures not supplemented with HGFs produced approximately 1 and 0.37 times the number of cells inoculated after 18 weeks, respectively. More importantly more than half of all cells removed from these unsupplemented cultures came from the first two samplings, indicating that many of these cells were from the original inoculum and that supplementation of the cultures with HGFs are required to induce significant cycling of progenitor and stem cells.

Morphologic analysis of nonadherent cells: The addition of multiple HGFs also increased the variety of myeloid cells produced in the cultures. The control cultures produced nonadherent cells that were predominately macrophages after week 3 in the culture. Production of erythroid cells decreased rapidly with few erythroid cells detected after week 5. The cultures containing Epo (Epo alone, IL-3+Epo, and IL-3+GM-CSF+Epo) produced a transient increase in erythroid cell production, with a high percentage (55–75%) of nonadherent cells being erythroid through week 3. When IL-3+Epo±GM-CSF was present, the cultures continued to produce erythroid cells throughout the 16 weeks in culture with about 5–15% of the nonadherent cells being typed as erythroid. Thus, in the presence of IL-3+Epo, erythropoiesis was active throughout. IL-3±Epo led to a nonadherent cell population that was predominately (60–70%) late granulocytes (LG) at week 5. The percentage of LGs steadily declined until it reached about 20% at week 18. The production of macrophages rose correspondingly. When GM-CSF was added to IL-3±Epo, the high percentage of LG persisted through 18 weeks. The combination of IL-3+GM-CSF thus led to active granulopoiesis for 18 weeks in culture, and the addition of Epo maintained erythropoiesis as well. Photomicrographs of the control and IL-3+GM-CSF+ Epo supplemented cultures at 5.5 weeks in culture show the dramatic enhancement in culture density and variety of-cells produced.

Kinetics of nonadherent progenitor cell production: Progenitor cell production increased with the addition of multiple HGFs. The production of granulocyte macrophage colony forming units (CFU-GMs) in the untreated controls was prolonged and steady for over 18 weeks, which is consistent with the earlier results obtained using rapidly perfused LTBMC without HGF. CFU-GM produced in the IL-3+GM-CSF and IL-3+Epo±GM-CSF cultures was approximately 10-fold higher than controls during weeks 3 to 5.

Erythroid burst forming unit (BFU-E) production in human LTBMC has been reported to be low and cease quickly (Coutinho et al, *Blood* (1990) 75(11): 2118–2129). The rapidly exchanged, untreated controls exhibited a rapid decrease in BFU-E production although low levels of BFU-E were produced through 17 weeks in culture. The addition of Epo alone did not significantly influence the number of BFU-Es produced. IL-3 alone induced a mild short-lived stimulation of BFU-E production in weeks 3–5. On the other hand, in the present cultures, IL-3 plus either Epo or GM-CSF induced a 10 to 20-fold elevation in the generation of nonadherent BFU-E compared to that of controls during weeks 3 to 5 of culture.

Discussion

It is clear from the data presented that, when combined with the inventive rapid exchange/perfusion hematopoietic cell culture conditions (Example 1), supplementation with judicious combinations of hematopoietic growth factors leads to increased production of specific lineages of cells. In this example IL-3+Epo resulted in sustained red cell production not previously observed in any human LTBMC. Similarly, IL-3+GM-CSF supplementation resulted in sustained granulocyte production. Supplementation with different HGFs may likewise lead to preferential production of different blood cells, such as platelets, B lymphocytes or T lymphocytes. The critical feature of the present invention is that the combination of rapid medium exchange conditions combined with hematopoietic growth factor supplementation results in essentially physiologic hematopoiesis, allowing the controlled in vitro generation of blood cells of the desired lineage or lineages.

The novelty of the present discovery is evident by comparison with other recent reports (Coutinho et al, Blood (1990) 75(11): 2118–2129). In these studies evaluating the effect of supplementation of slowly exchanged LTBMCs with HGFs, although cell production increases over untreated controls with addition of HGFs, the increases are smaller and shorter in duration than are reported here. This discrepancy suggests that physiologic perfusion stimulates hematopoiesis via a mechanism independent of, and synergistic with, the effects of IL-3, GM-CSF, or Epo. For example, as disclosed in the previous parent patent application, increased serum/medium perfusion rates can induce production of endogenous hematopoietic growth factors by stromal cells in vitro. Increased medium perfusion and addition of HGFs may therefore also induce other HGF production (e.g. kit-ligand) by stimulating hematopoietic or accessory cells in the cultures. Therefore, increasing the medium perfusion rate may provide LTMBCs benefits other than just increasing metabolite and decreasing waste product levels.

Example 3

Use of Rapid Exchange Culture System to Deplete a Bone Marrow Cell Population of Lymphoid Cells The inventors have discovered that the present methods, including the present culture media conditions, which allow for the in vitro replication and differentiation of human stem and hematopoietic progenitor cells can simultaneously promote the disappearance of specified cells present in the original composition, notably lymphoid cells such as T-cells and B-cells. Although the present methods and composition support the replication and differentiation of human stem and hematopoietic progenitor cells, human T-cells and B-cells do not proliferate or maintain viability in these in vitro culture conditions.

Therefore, in accordance with this embodiment of the invention, a mixed human hematopoietic mononuclear cell fraction can be effectively depleted of T-cells and/or B-cells, under conditions which allow for expansion of stem and progenitor cells. This method of selective T-cell depletion of human hematopoietic cell populations has notable therapeutic value as noted above.

Methods: The Conditions of Culture are identical to those in Example 2.

Analysis of B-cells, T-cells, and early Hematopoietic Cells: At weekly intervals, cells were removed from the cultures and analyzed by flow cytometry on a FACS Scan (Becton-Dickinson) Cell Analyzer. B-cells were enumerated with anti-CD19, T-cells with anti-CD3, and early hematopoietic progenitor cells with anti-CD34, using fluoresceinated normal mouse Ig as a background control (all antibodies were from Becton-Dickinson, Inc).

Results: Human bone marrow cells were cultured as in Example 2, above. Samples were removed prior to the culture and following 7, 14 and 21 days of culture. Aliquots of $2 \times 10^5$ cells each were analyzed for the presence of either CD-3, -19, or -34, and % +cells were determined by subtracting background fluorescence with a fluoresceinated normal mouse Ig control antibody. As shown in Table 3 below, T-cells and B-cells were rapidly lost in these cultures, while primitive hematopoietic progenitor (CD34+) cells were maintained:

TABLE 3

Selective Depletion of T and B Lymphocytes from within a Proliferating Human Bone Marrow Culture.

| | % of Cells in Culture Week | | | |
|---|---|---|---|---|
| Cell Subset | 0 | 1 | 2 | 3 |
| T-cell (CD-3) | 20.8 | 11.2 | 8.2 | 0.1 |
| B-cell (CD-19) | 5.6 | 3.0 | 1.2 | 0.0 |
| Progenitor cell (CD-34) | 0.4 | 0.7 | 0.7 | 0.7 |

Thus, the described culture conditions support the survival and proliferation of hematopoietic progenitor cells, while simultaneously depleting the culture of T and B lymphocytes. Human hematopoietic cell populations prepared in this way are directly applicable to allogeneic bone marrow transplantation, and also to depletion of virally infected T-and/or B-cells from a hematopoietic cell population for auto-or allo-transplantation.

Example 4

Use of Rapidly Exchanged/perfused Culture System to Deplete a Hematopoietic Cell Population of Tumor Cells In a fashion analagous to that of lymphoid cell depletion, cancer cells, including T- and B-cell leukemia and lymphoma cells, and chronic myelogenous leukemia cells, can be depleted from within a hematopoietic cell population by cultured in a rapid medium exchanged system. The essential feature of the culture system, that it allows the survival and proliferation of hematopoietic stem and progenitor cells while not supporting the survival and proliferation of other cell types, results in the loss of cancer cells which are relatively fastidious in their growth and survival requirements.

By example, chronic myelogenous leukemia cells (CML) can be depleted from within a bone marrow cell culture that contains normal and CML cells, over a culture period of 14–21 days. Under these conditions, the % of cultured cells that belong to the CML clone can decrease from 90% or more to under 5%, and in some cases less than 1%.

In this way the presently described culture system can be directly applicable to the purging of cancer cells from within any hematopoietic cell mass (bone marrow, peripheral blood, cord blood, fetal blood) for autologous or allogeneic bone marrow transplantation, and can be applied directly to the treatment of cancer patients.

The exact time of culture required to achieve substantial depletion of the malignant cells may depend on the exact type and the number of malignant cells present. However, the time required to achieve a culture substantially free of any particular type of malignant cell may be easily determined by one of skill in the art by using the present method in conjunction with any conventional assay for the type of malignant cell in question.

Example 5

Use of Rapidly Exchanged/perfused System to Assay the Influence of Specified Molecules on Hematopoiesic We now demonstrate how the culture system described in Example 2 can be used to assay the effects of any individual or combination of additional specified substances. In this embodiment, this system provides a method for assaying the affect of a substance or substances on a hematopoietic cell culture. In accordance with this embodiment, one adds to a cell culture carried out in accordance with the invention at least one substance suspected of having an affect, which may be either beneficial or detrimental, on the cell culture. One then compares the cell culture profile obtained in the absence of the substance being tested to the cell culture profile obtained in the presence of the substance. This embodiment may be used in accordance with the various embodiments used in the present invention to ascertain the particular affect of a suspected substance on a human stem or hematopoietic cell system. As examples, Interleukin 6 (IL-6) and Granulocyte colony stimulating factor (G-CSF), are two hematopoietic growth factors with well described hematopoietic activities on already-developed progenitor cells. The present assay system provides an improved approach to analyzing the effects of these HGFs along with those of IL-3 and GM-CSF, both on progenitor cells and on primitive hematopoietic progenitor cells.

Materials and Methods

Cells, hematopoietic progenitor cell assays, LTBMCs, and statistical analyses were as in Example 1.

Hematopoietic growth factors: IL-3, 1 ng/ml; GM-CSF, 1 ng/ml of GM-CSF; Epo, 0.1 U/ml; IL-6, 10 U/ml (Collaborative Research Inc.), and G-CSF, 0.1 ng/ml (Amgen Biologicals).

Results:

Kinetics of nonadherent cell production: Supplementation of IL-6 or G-CSF to the combination of IL-3+GM-CSF+Epo reduced the number of granulocytes produced. IL-3+GM-CSF+Epo with IL-6 or G-CSF resulted in an approximate 2-fold decrease in late granulocyte production similar to the reduction seen in early granulocyte production. Interestingly, macrophage production through 6.5 weeks in culture was not significantly affected by any combination of growth factor supplementation in the LTBMCS. Cumulative macrophage production varied between 0.84 and $1.4 \times 10^6$ cells per culture for the untreated and HGF supplemented cultures (Table 4).

TABLE 4

Cumulative cell production by cell lineage in growth factor supplemented LTBMCs over the first 6.5 weeks of culture.

| Culture | Erythroid (E) | Early Granulo- cytes (EG) | Late Granulo- cytes (LG) | ratio (LG/ EG) | Macro- phages (Mo) |
|---|---|---|---|---|---|
| control | 0.41 | 0.76 | 1.6 | 2 | 0.84 |
| IL-3 | 0.14 | 3.0 | 3.1 | 1 | 2.9 |
| GM-CSF | 0.11 | 2.7 | 6.8 | 2.5 | 2.1 |
| IL-3 + GM-CSF | 0.04 | 4.5 | 11.9 | 2.5 | 1.2 |
| IL-3 + GM-CSF + Epo | 3.40 | 4.7 | 11.8 | 2.5 | 1.4 |
| IL-3 + GM-CSF + Epo + IL-6 | 3.50 | 3.2 | 6.9 | 2 | 1.4 |
| IL-3 + GM-CSF + Epo + G-CSF | 3.10 | 3.4 | 6.9 | 2 | 1.6 |

The data in Table 4 clearly shows the effects of the growth factors on the kinetics of lineage production in the cultures. For instance, by comparing the cumulative production of erythroid cells in the IL-3+GM-CSF and IL-3+GM-CSF+Epo supplemented cultures (lines 4 and 5 in Table 4) one can clearly assay for the effects of Epo on the reconstitution of erythropoiesis in vitro. Both of these cultures produce the same number of granulocytes and macrophages but they differ vastly in their production of erythroid cells. The culture with Epo produced 3.4 million cells while the one without Epo produces undetectable amounts of erythroid cells. Similarly, by comparing lines 5 and 6 in table 4 one can evaluate the influence of IL-6 on lineage productivities. IL-6 does not influence the production of erythroid cells but diminishes the number of early granulocytes produced and their maturation to late granulocytes.

In an analogous fashion, one can use this in vitro tissue system as an assay system for the effects of synthetic and/or natural substances on lineage reconstitution or depletion as well as the survival (or purging) of malignant cells in (from) populations of bone marrow cells.

Progenitor cell production: Progenitor cell production was dramatically influenced by addition of HGFs to LTB-MCs. Granulocyte macrophage progenitor cell (CFU-GM) production was also affected by HGF supplementation of the LTBMCs. Individually, IL-3 or GM-CSF produced only a slight increase in total CFU-GM (Table 5) whereas IL-3+GM-CSF+Epo induced approximately a 1.7-fold increase in total CFU-GM production. IL-3+GM-CSF+Epo with IL-6 or G-CSF induced a 2.4 and 3.1-fold increase in the number of CFU-GM removed from culture, respectively. These results suggest that IL-3 and GM-CSF act synergistically to recruit early myeloid cells into the granulocyte and macrophage lineages and that Epo has little effect on CFU-GM production. Interestingly, IL-6 and more significantly G-CSF when combined with IL-3+GM-CSF+Epo, had a large positive effect on the number of CFU-GM when removed from culture whereas they had little effect in the erythroid lineages as shown by BFU-E production suggesting a more restricted action of these HGFs.

CFU-GEMM production was significantly influenced by HGF supplementation. Individual supplementation of the LTBMCs with either IL-3 or GM-CSF alone, increased the number of CFU-GEMM removed from culture 1.8 and 1.6 fold, respectively. However, combinations of CSFs induced a much larger increase in CFU-GEMM production than did either IL-3 or GM-CSF alone. Supplementation with IL-3+GM-CSF and IL-3+GM-CSF+Epo induced a 3.5 and 10.3-fold increase in the total number of CFU-GEMM removed, suggesting that Epo plays either a direct or indirect role in early hematopoietic events. The addition of IL-6 or G-CSF to the combination of IL-3+GM-CSF+Epo did not affect CFU-GEMM production above IL-3+GM-CSF+Epo alone (Table 5).

TABLE 5

The cumulative number of progenitor cells removed from rapidly perfused HGF supplemented human long-term bone marrow cultures.

| culture | BFU-E | CFU-GM | CFU-GEMM |
|---|---|---|---|
| control | 700 | 1900 | 50 |
| IL-3 | 1900 | 2100 | 90 |
| GM-CSF | 800 | 2200 | 80 |
| IL-3 + GM-CSF | 2500 | 3200 | 200 |
| IL-3 + GM-CSF + Epo | 3000 | 3200 | 500 |
| IL-3 + GM-CSF + Epo + IL-6 | 3200 | 4600 | 500 |
| IL-3 + GM-CSF + Epo + IL-6 or G-CSF | 3200 | 5900 | 500 |

Production of Progenitor Cells from Stem Cells. Although the most primitive hematopoietic cells that can be directly assayed are the progenitor cells; CFU-GEMM, CFU-GM, and BFU-E, the presence and activity or earlier stem cells can be inferred by the continued production of progenitor cells. Thus, progenitor cell production is an indirect measure of primitive stem cell activity. One can assay stem cells, therefore, by analyzing the kinetics of the progenitor cell pool. The four process rates that determine the progenitor cell pool size are:

$V_1$: The rate of production of progenitor cells by more undifferentiated stem cells;

$V_2$: The rate of loss of progenitor cells through the act of sampling of nonadherent cells from the culture;

$V_3$: The rate of loss of progenitor cells by their differentiation to mature cells of a particular lineage;

$V_4$: The rate of death of progenitor cells. The initial number, $C_0$, of each progenitor cell species can be determined by assay at culture initiation.

The question that we wish to answer is; Are stem cells being stimulated to produced progenitor cells—i.e. is $V_1$ greater than zero? Cell death, $V_4$, cannot be assessed. $V_2$ however, can be measured by assaying the nonadherent cells removed from culture, and $V_3$ can be estimated from nonadherent cell production data. A conservative estimate of the rate of progenitor cell differentiation, $V_3$, can be determined by assuming that each progenitor cell has 10 divisions remaining to become a terminally differentiated cell. Therefore, each progenitor cell is equivalent to $2^{10}$ (1024) mature cells. From the total number of mature cells produced of a specific lineage, the number of progenitor cells (BFU-E and CFU-GM) that differentiated can be back-calculated. Therefore, if the removal and differentiation of progenitor cells $(V_2+V_3)$ exceeds the numbers of progenitor cells inoculated, $C_o$, then progenitor cells must have been produced, and $V_1$ is greater than zero.

We applied these calculation to two measured progenitor cell pools, CFU-GM and BFU-E. Tables 6 and 7 show that only in the cultures supplemented with IL-3+GM-CSF+Epo, IL-3+GM-CSF+Epo+IL-6, or IL-3+GM-CSF+Epo+G-CSF did the total number of BFU-E that could be measured (those that were removed and those that differentiated) in culture exceed those inoculated. In these cultures, the removal of BFU-E was approximately equivalent to those that differentiated (Table 5). Similar calculations for CFU-GM show that production of CFU-GM (Table 6) was greater than zero ($V_1$ >0) in all cultures. However, IL-3+GM-CSF or IL-3+GM-CSF+Epo supplementation induced a 5.1-fold increase in CFU-GM production over the control cultures which itself was 8.4-fold greater than the inoculum. Thus the combination of IL-3 and GM-CSF stimulated the differentiation of stem cells to progenitor cells.

TABLE 6

The cumulative production of BFU-E removed and differentiated in growth factor supplemented rapidly perfused human long-term bone marrow cultures.

| Culture | Number of BFU-E removed (plated) ($V_3$) | Number of erythroid cells removed ($\times 10^4$) ($V_3$) | Estimated number of BFU-E that differentiated ($V_3$) | Total number of BFU-E ($V_3$) |
|---|---|---|---|---|
| Inoculum | (2900) | (0) | (0) | (2900) |
| control | 700 | 0.4 | 400 | 1100 |
| IL-3 | 1900 | 0.1 | 100 | 2000 |
| GM-CSF | 800 | 0.1 | 100 | 900 |
| IL-3 + GM-CSF | 2500 | 0.0 | 0 | 2500 |
| IL-3 + GM-CSF + Epo | 3000 | 3.4 | 3400 | 6400 |
| IL-3 + GM-CSF + Epo + IL-6 | 3200 | 3.5 | 3500 | 6700 |
| IL-3 + GM-CSF + Epo + G-CSF | 3200 | 3.1 | 3100 | 6300 |

Every fourth biweekly sampling from the cultures was assayed for BFU-E and the non-assayed values were estimated by linear interpolation between two known data points ($V_2$).

Discussion: The example extends our understanding and use of the prolific rapidly perfused HGF supplemented human LTBMCs described in Examples 1 and 2. We have outlined the kinetics of lineage reconstitution in this culture system and have shown how HGF supplementation influences mature and progenitor cell production.

Although there are many uses of this system for the analysis of the effects of added substances, for this example we focus on the analysis of the effects of IL-6 and G-CSF versus GM-CSF+IL-3+Epo on progenitor cell production from stem cells. A population balance analysis of the progenitor and nonadherent cell production data showed that progenitor cells can be produced in HGF supplemented rapidly perfused LTBMCs. This analysis showed that all rapidly perfused cultures produced CFU-GM although the number of CFU-GM produced is strongly growth factor dependent. BFU-E, on the other hand, were only produced in the cultures supplemented with (IL-3+GM-CSF+Epo)+ IL-6 or +G-CSF. Analysis of CFU-GM production alone would indicate that the cultures supplemented with IL-3+ GM-CSF+Epo and either IL-6 or G-CSF stimulated CFU-GM production more than the combination of IL-3+GM-CSF+Epo alone. However, a population balance of the total CFU-GM production (Table 7), shows that IL-6 and G-CSF did not induce increased CFU-GM production over the combination of IL-3+GM-CSF+Epo. Instead, this analysis suggests that the effect IL-6 and G-CSF on the CFU-GM pool was to change the cells from a more adherent compartment to a less adherent compartment, making the cells available for removal during the bi-weekly sampling. This analysis shows that both differentiation and sampling must be taken into account to better understand the effect of growth factors on progenitor cell production.

In summary, this example demonstrates how the rapid medium exchange/perfusion hematopoietic cultures allow for the precise analysis of the hematopoietic activity of added molecules, particularly in regard to their effects on hematopoietic stem cells. This system can be used to analyze the hematopoietic activity of any desired soluble substance or substances.

liquid medium may be pumped with a syringe pump that may be located in a refrigerator adjacent to an incubator, maintained at a temperature sufficient to sustain hematopoiesis. The fresh medium may be kept at 4° C. preventing decay of chemically unstable medium components such as glutamine and growth factors. The medium may be fed through a PharMed tubing (Norphrene based tubing). This tubing may have a "slack" so that the syringe pump can be moved to a laminar flow hood where the syringes can be replaced in a sterile environment. The extra tubing may be kept in the refrigerator so that only a short tube segment is at room or at incubator temperature. This arrangement is important since liquid residence time in the tube can be on the order of days (depending of the flow rate used).

The gas may come from either a cylinder containing premixed gases (a mixture of $O_2$, $N_2$ and $CO_2$) or may be simply taken from the inside of the incubator (a mixture of air and $CO_2$). The flowrate and composition of the gas stream may thus be easily controlled. The gas may be pumped with an aquarium pump through a sandstone in a 100 ml medium flask to give relative humidities as close to 100% as possible. The gas line may contain a sterile filter.

The spent medium may be collected in a 100 ml medium bottle. Samples may be taken from it for analysis of medium components. The sets of chambers may be kept in an $CO_2$ incubator with a humidification system.

Component Description

Perfusion Chamber. The perfusion chamber may be made from two specially machined pieces of a polycarbonate slab, the chamber top and bottom. Between the top and bottom piece two identical ¼ inch silicone rubber gaskets may be placed.

When the chamber is assembled, a membrane may be placed between the two silicone gaskets which in turn may be placed between the top and bottom piece and four bolts may be used to hold the chamber together. The difference between the top and bottom piece is the number of ports provided. The bottom piece may have two ports for gas inlet

TABLE 7

The cumulative production of CFU-GM removed and differentiated in growth factor supplemented rapidly perfused human long-term bone marrow cultures.

| Culture | Number of CFU-GM removed (plated) ($V_2$) | Number of GM cells removed (×10⁴) ($V_3$) | Estimated number of CFU-GM that differentiated ($V_3$) | Total number of CFU-GM ($V_3$) |
|---|---|---|---|---|
| Inoculum | (2500) | (0) | (0) | (2900) |
| control | 1900 | 3.2 | 3200 | 4100 |
| IL-3 | 2100 | 9.0 | 9000 | 11,100 |
| GM-CSF | 2200 | 11.7 | 11,700 | 13,900 |
| IL-3 + GM-CSF | 3200 | 17.6 | 17,600 | 20,800 |
| IL-3 + GM-CSF + Epo | 3200 | 17.9 | 17.000 | 20,200 |
| IL-3 + GM-CSF + Epo + IL-8 | 4600 | 11.5 | 11,500 | 16,100 |
| IL-3 + GM-CSF + Epo + G-CSF | 5900 | 11.9 | 11,900 | 17,800 |

Every fourth biweekly sampling from the cultures was assayed for CFU-GM and the non assayed values were estimated by linear interpolation between two known data points ($V_3$).

Functioning, Reconstructed in vitro Bone Marrow Culture Process Flowsheet

A process for the carrying out the present invention will now be described in relation to a preferred embodiment. The and outlet, whereas the top piece may have three ports, a medium inlet and outlet and a sample port, placed in the middle of the top piece. The outlet port may be constructed so that an angle is formed relative to the horizontal position to provide gravity induced settling for any non-adherent cells that might be floating about the chamber. The geometry of the hole in the silicone gasket may be circular, but an elliptical shape with the inlet and outlet ports placed in focal points of the ellipse may provide a better fluid distribution.

To provide for gas mass transfer, cell/extra-cellular matrix attachment and to prevent water leakage a two membrane system may be used. The lower membrane may be a gas exchange membrane, such as silicone, teflon, mylar, etc. The membrane is preferably hydrophobic to prevent loss of water and is permeable to gases. Furthermore, the gas exchange membrane can provide a mechanical support for the second membrane. The second membrane is for cell attachment and growth and may be, e.g., an inorganic ceramic based membrane. It can be coated with extra-cellular protein. We have used the PepTite-20000 RGD based adhesion protein (a product of Telios Pharmaceutical, Inc., San Diego, Calif.) successfully for this purpose. Further, a highly desirable property of a ceramic inorganic membrane is that it becomes transparent upon hydration thus making microscopic observation of the cells possible. The second membrane may serve as a surface for the attachment of the adherent cells.

The only difficulty encountered with the two membrane system arises from the fact that the thermal expansion coefficient for the inorganic membrane exceeds that of other chamber components. Thus, during autoclaving the bolts that hold the chamber together cannot be tightened. Even with loose bolts, we have experienced that about 20% of the chambers have a cracked inorganic membrane after autoclaving.

The tubing for medium and gases may be connected to the top and bottom pieces using polypropylene fittings and Luer Locks rings. By employing silicone O-rings, good seals are formed and no leakage problems have occurred.

The perfusion chamber can be assembled in other configurations. Two alternatives are:

(1) An inverted configuration. The configuration described above is inverted, and the cells grow on the bottom plate. In this case, only the gas exchange membrane is required; and (2) A three-chamber design. Gas is circulated through a top compartment which is separated from a central compartment by a gas exchange membrane. The cells are in the central compartment which is separated from a bottom compartment by a cell growth membrane. The central compartment is stagnant, while the bottom compartment is continuously perfused.

Auxiliary Components. The syringe pump should carry up to ten syringes (for a set of ten parallel chambers) of the appropriate size. Currently we are using a flowrate of 2 ml/day and 10 ml syringes, requiring syringe change every 5 days. The pump should be accurate, reliable, and be able to operate at 4° C. over extended periods of time. We have used a Harvard '22' syringe pump with a multiple syringe holder. These pumps have proved satisfactory, although twice they have broken down after long periods of use at 4° C.

The air may be pumped with an aquarium pump. Medium bottles may be used for the spent medium and for the humidification of the incoming gas stream. Each component is subject to modifcation. For the spent medium bottle, e.g., one can add a septum that would allow for sterile sampling or depletion of the spend medium. A tall and narrow bottle might be preferable for humidifying a stream of premixed gases since they are at very low relative humidity. When air from the incubator is used this precaution is not necessary since the incubator air is at high relative humidity.

Operating Procedures

Starting Up the Perfusion Chambers

Cells. The cells are treated prior to inoculation in the same fashion as they are prepared for Dexter cultures. After aspiration from a donor, mononuclear cells are separated on a discontinuous density gradient (Ficoll) and then washed several times in the culture medium. This procedure typically takes about half a day.

Medium. The medium used is the standard Dexter medium, 10% horse serum, 10% fetal calf serum, $10^{-6}$ M hydrocortisone and IMDM. In addition, hematopoietic growth factors are added. Typically, Il-3, GM-CSF and Epo are used as previously described. The search continues for the optimal combination of added hematopoietic factors.

Perfusion Chambers. The preparation of the perfusion chambers starts one day prior to inoculation. Assembly of a set of 6–10 perfusion chambers takes about 6 to 8 hours. This involves sizing/cutting tubing, putting fittings into the chamber, preparing the medium bottles, etc. At the end of the day the full chamber assembly (less the tubing and attachments for the gas exchange) is autoclaved without medium (all components are autoclaved). The set of chambers is then typically stored in a hood overnight. The following day the full set of components is assembled in the hood, the medium introduced, any adhesion protein applied, cells inoculated, the chambers placed in the incubator, the syringes loaded into the pump and stored in the refrigerator. If cell preparation is included, these steps take another day. Thus, the chambers are running at the end of the second say. The perfusion typically begins after the cells have settled in the chamber for 12 to 24 hours.

Running the Perfusion Chambers

Once the chambers are set up they are easy to maintain; the syringes need to be replaced at a fixed interval and non-adherent cells collected.

Replacing Syringes. The syringes are typically replaced on a fixed schedule. For instance, during the initial runs with the chambers, 10 ml syringes were used at a flow rate of 2 mls per day. Syringes thus were replaced every 5th day. The syringe pump is moved from the incubator to the hood where the syringes are replaced in a sterile environment. This transfer of the pump is allowed by the "slack" in the medium inlet line as described above. We have yet to experience contamination problems during this procedure.

Microscopic observation. The top and bottom of the perfusion chamber and the teflon membrane are transparent. The inorganic membrane becomes transparent once it is hydrated and thus during operation one can observe the cells in the chamber through a microscope. To do so one needs a long distance objective.

Sampling cells. Sampling the cells from the chambers can be achieved using one of two methods. Firstly, we let cells settle by gravity inversion for two hours and then we replace 2 mls in the chamber by pushing liquid through the inlet port and collecting it from the outlet line. Secondly, we have pulled directly through the sampling port 2 mls leaving air space in the chamber that then disappears within a day due to the incoming medium. The second method is more invasive and yields a higher number of cells (approximately two to four fold).

The cell sampling takes place in the laminar flow hood. The set of chambers is moved from the incubator to the hood and the length of the inlet medium line allows for this transfer. Since the solubility of oxygen is higher at lower temperatures, the cooling to room temperature often results in the formation of bubbles in the chambers (the bubbles are often located between the two membranes) once they are returned to the incubator. Such bubbles disappear after readjustment to 37° C.

The adherent cells can be removed in a similar fashion after treatment with trypsinization.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. In a method of bone marrow transplantation, comprising obtaining a bone marrow tissue or blood sample from a donor, culturing said bone marrow tissue or blood sample, and implanting said bone marrow tissue or blood sample in a donee, wherein the improvement is said culturing comprises culturing said bone marrow tissue or blood sample, which comprises a mass of human stromal cells, in a liquid culture medium which is replaced, either continuously or periodically at a rate of about 1 ml of medium per ml of culture per about 24 to about 48 hour period, and removing metabolic products and replenishing depleted nutrients while maintaining said culture under physiologically acceptable conditions.

2. The method of claim 1, wherein said donee is said donor.

3. The method of claim 1, wherein said donee is not said donor.

4. The method of claim 1, wherein said blood sample comprises a human cord blood sample.

5. The method of claim 1, wherein said human stromal cells are human bone marrow stromal cells.

6. The method of claim 1, wherein GM-CSF is added to said medium.

7. The method of claim 1, wherein IL-3 and GM-CSF is added to said medium.

* * * * *

UNITED STATES PATENT AND TRADEMARK OFFICE
CERTIFICATE OF CORRECTION

| | | |
|---|---|---|
| PATENT NO. | : 6,667,034 B2 | |
| APPLICATION NO. | : 08/857594 | |
| DATED | : December 23, 2003 | |
| INVENTOR(S) | : Bernhard O. Palsson et al. | |

It is certified that error appears in the above-identified patent and that said Letters Patent is hereby corrected as shown below:

Column 5, line 48, "stude" should read --study--.

Column 7, line 51, "metobolism" should read --metabolism--.

Column 8, line 10, "suprisingly" should read --surprisingly--;

line 12, "comprises" should read --comprise--.

Column 9, line 21, "multiplicity or" should read --multiplicity of--.

lines 36-37, "Lactacte concentration is generally in the range of from about 1 to 3mM." should read --Lactate concentration is usually maintained below 35mM. Glutamine concentration is generally maintained in the range of from about 1 to 3 mM.--.

Column 10, line 1, "infection was" should read --infection of cells. Earlier systems in which retroviral infection--;

line 2, "preset" should read --present--;

line 16, "increase" should read --increased--.

Column 11, line 70, "62.47" should read --62.57--.

Column 12, line 50, "326-1968" should read --320-1968--.

Column 15, line 9, "Mg" should read --mg--;

line 50, "330-6600" should read --320-6600--.

Column 16, line 9, "Mg" should read --mg--.

Column 17, line 7, "30000.0" should read --3000.00--.

Column 18, line 54, "cited refer" should read --cited in references--.

| Minimum Essential Media (MEM)[1] | | | | | | |
|---|---|---|---|---|---|---|
| COMPONENT | 410-1700 Powder mg/L | 320-1890 1X Liquid mg/L | 320-1096 1X Liquid mg/L | 410-2400 Powder mg/L | 320-1097 1X Liquid mg/L | 410-2500 Powder mg/L |
| INORGANIC SALTS: | | | | | | |
| $CaCl_2$ (anhyd.) | 200.00 | 200.00 | 200.00 | 200.00 | 200.00 | 200.00 |
| KCl | 400.00 | 400.00 | 400.00 | 400.00 | 400.00 | 400.00 |
| $MgSO_4$ (anhyd.) | 97.67 | — | — | 97.67 | — | 97.67 |
| $MgSO_4 \cdot 7H_2O$ | — | 200.00 | 200.00 | — | 200.00 | — |
| NaCl | 6800.00 | 6800.00 | 6800.00 | 6800.00 | 6800.00 | 6800.00 |
| $NaHCO_3$ | — | 2200.00 | 1500.00 | — | 2200.00 | — |
| $NaH_2PO_4 \cdot H_2O$[a] | 140.00 | 140.00 | 140.00 | 140.00 | — | — |
| OTHER COMPONENTS: | | | | | | |
| D-Glucose | 1000.00 | 1000.00 | 1000.00 | 1000.00 | 1000.00 | 1000.00 |
| HEPES | — | — | — | — | — | — |
| Lipoic acid | — | — | — | — | — | — |
| Phenol red | 6.0 | 10.00 | 10.00 | 10.00 | 10.00 | 10.00 |
| Sodium pyruvate | — | — | — | — | — | — |
| Sodium succinate | 100.00 | — | — | — | — | — |
| Succinic acid | 75.00 | — | — | — | — | — |
| AMINO ACIDS: | | | | | | |
| L-Alanine | — | — | — | — | — | — |
| L-Arginine | — | — | — | — | — | — |
| L-Arginine.HCl | 126.00 | 126.00 | 126.00 | 126.00 | 126.00 | 126.00 |
| $L\text{-Asparagine} \cdot H_2O$ | — | — | — | — | — | — |
| L-Aspartic acid | — | — | — | — | — | — |
| L-Cystine | — | 24.00 | — | — | 24.00 | — |
| L-Cystine.2HCl | 31.00 | — | 31.00 | 31.29 | — | 31.29 |
| $L\text{-Cysteine.HCl} \cdot H_2O$ | — | — | — | — | — | — |
| L-Glutamic acid | — | — | — | — | — | — |
| L-Glutamine | — | — | — | 292.00 | 292.00 | 292.00 |
| Glycine | — | — | — | — | — | — |
| L-Histidine | — | — | — | — | — | — |
| $L\text{-Histidine.HCl} \cdot H_2O$ | 42.00 | 42.00 | 42.00 | 42.00 | 42.00 | 42.00 |
| L-Isoleucine | 52.00 | 52.00 | 52.00 | 52.00 | 52.00 | 52.00 |
| L-Leucine | 52.00 | — | 52.00 | — | 52.00 | 52.00 |
| L-Lysine | — | — | — | — | — | — |
| L-Lysine.HCl | 72.50 | 72.50 | 72.50 | — | 72.50 | 72.50 |
| L-Methionine | 15.00 | 15.00 | 15.00 | — | 15.00 | 15.00 |
| L-Phenylalanine | 32.00 | 32.00 | 32.00 | 32.00 | 32.00 | 32.00 |
| L-Proline | — | — | — | — | — | — |
| L-Serine | — | — | — | — | — | — |
| L-Threonine | 48.00 | 48.00 | 48.00 | 48.00 | 48.00 | 48.00 |
| L-Tryptophan | 10.00 | 10.00 | 10.00 | 10.00 | 10.00 | 10.00 |
| L-Tyrosine | 36.00 | 36.00 | — | — | 36.00 | — |
| $L\text{-Tyrosine.2Na} \cdot 2H_2O$ | — | — | 51.90 | 51.90 | — | 51.90 |
| D-Valine | — | — | — | — | — | — |
| L-Valine | 46.00 | 46.00 | 46.00 | 46.00 | 46.00 | 46.00 |
| VITAMINS: | | | | | | |
| L-Ascorbic acid | — | — | — | — | — | — |
| Biotin | — | — | — | — | — | — |
| D-Ca pantothenate | 1.00 | 1.00 | 1.00 | 1.00 | 1.00 | 1.00 |
| Choline bitartrate | 1.80 | — | — | — | — | — |
| Choline chloride | 1.00 | 1.00 | 1.00 | 1.00 | 1.00 | 1.00 |
| Folic acid | 1.00 | 1.00 | 1.00 | 1.00 | 1.00 | 1.00 |
| i-Inositol | 2.00 | 2.00 | 2.00 | 2.00 | 2.00 | 2.00 |
| Niacinamide | 1.00 | 1.00 | 1.00 | 1.00 | 1.00 | 1.00 |
| Pyridoxal.HCl | 1.00 | 1.00 | 1.00 | 1.00 | 1.00 | 1.00 |
| Riboflavin | 0.10 | 0.10 | 0.10 | 0.10 | 0.10 | 0.10 |
| Thiamine.HCl | 1.00 | 1.00 | 1.00 | 1.00 | 1.00 | 1.00 |
| Vitamin $B_{12}$ | — | — | — | — | — | — |
| RIBONUCLEOSIDES: | | | | | | |
| Adenosine | — | — | — | — | — | — |
| Cytidine | — | — | — | — | — | — |
| Guanosine | — | — | — | — | — | — |
| Uridine | — | — | — | — | — | — |
| DEOXYRIBONUCLEOSIDES: | | | | | | |
| 2' Deoxyadenosine | — | — | — | — | — | — |
| 2' Deoxycytidine.HCl | — | — | — | — | — | — |

| Minimum Essential Media (MEM)[1] | | | | | | | |
|---|---|---|---|---|---|---|---|
| 2' Deoxyguanosine | — | — | — | — | — | — |
| Thymidine | — | — | — | — | — | — |

[1] Eagle, H. (1959) Science, 130, 432.
[2] Nature, New Biology (1971) 230, 310.
[*] Original formula lists this component as $NaH_2PO_4 \cdot 2H_2O$.

UNITED STATES PATENT AND TRADEMARK OFFICE
CERTIFICATE OF CORRECTION

PATENT NO. : 6,667,034 B2
APPLICATION NO. : 08/857594
DATED : December 23, 2003
INVENTOR(S) : Bernhard O. Palsson et al.

It is certified that error appears in the above-identified patent and that said Letters Patent is hereby corrected as shown below:

Column 19, line 6, "370-1955" should read --330-1955--;

Line 6, "380-3990" should read --380-2390--;

lines 5-6, "430-1300" should read --430-1200--;

line 12, "0.025   0.0025" should read --0.025   0.0025   0.0025--;

line 14, "2150.00   215.00   283.00" should read

--2850.00   285.00   285.00--;

line 15, "13.00" should read --83.00--;

line 18, "152.00   1528.00   152.00" should read

--152.80   1528.00   152.80--;

line 22, "0.0218   0.283   0.0283" should read

--0.0288   0.288   0.0288   0.0288--;

line 24, "31000.00" should read --11000.00--;

line 25, "5950.00" should read --5958.00--;

line 29, "140" should read --1.20--;

line 36, "33.01" should read --15.01--;

line 37, "1.30.00   13.00   1.3.00" should read

--130.00   13.00   13.00--;

line 40, "7.31" should read --7.51--;

UNITED STATES PATENT AND TRADEMARK OFFICE
CERTIFICATE OF CORRECTION

PATENT NO.         : 6,667,034 B2
APPLICATION NO. : 08/857594
DATED                  : December 23, 2003
INVENTOR(S)        : Bernhard O. Palsson et al.

It is certified that error appears in the above-identified patent and that said Letters Patent is hereby corrected as shown below:

Column 19, line 42, "2.40  2.40" should read --2.60  2.60--;

line 44, "4.43" should read --4.48--;

line 45, "Pheuylalanine" should read --Phenylalanine--; same line "5.05" should read --5.00--;

line 46, "31.50" should read --11.50--;

line 47, "10.30" should read --10.50--;

line 48, "Tryptophaa" should read --Tryptophan--; same line "0.40" should read --0.60--;

line 50, "2.68" should read --2.61--;

line 53, "Biotia" should read --Biotin--;

line 54, "pantohenatee" to --pantothenate--;

line 55, ".0690  6.90  .0696 .0696 " should read --0.698  6.98  0.698  0.698--;

line 56, "13.29" should read --13.20--;

line 57, "Inosinol" should read --Inositol--, same line "0.341" should read --0.541--;

line 58, "Pyridine ACL OX6 2.00 0.376" should read --Pyridoxine HCL 0.206  2.06  0.206--

Column 19, line 59, "Riboflvin" should read --Riboflavin--; same line "3.74" should read --3.76--;

line 60, ".1.00" should read --1.00--;

line 66, "0.236" should read --0.238--.

UNITED STATES PATENT AND TRADEMARK OFFICE
CERTIFICATE OF CORRECTION

PATENT NO.       : 6,667,034 B2
APPLICATION NO. : 08/857594
DATED            : December 23, 2003
INVENTOR(S)      : Bernhard O. Palsson et al.

It is certified that error appears in the above-identified patent and that said Letters Patent is hereby corrected as shown below:

Column 21, line 7, "328.1855" should read --320-1855--;

line 12, "SALTs" should read --SALTS--;

line 24, "Glulathione" should read --Glutathione-- line 38, "L-Leucina" should read --L-Leucine--.

Column 22, line 7, "328-1855" should read --320-1855--;

line 17, "L-Threoaine" should read --L-Threonine--;

line 18, "L-Trypsophan" should read --L-Tryptophan--;

line 23, "Biota" should read --Biotin--;

line 25, "pantotbcnatc" should read --pantothenate--;

line 32, "Pyridoxime" should read --Pyridoxine--;

line 33, "0.20" should read --0.50--;

line 38, "Kitamurs" should read --Kitamura--;

Column 22, line 38, "Journel" should read --Journal--;

line 39, "2034" should read --2054--;

line 43, "1838" should read --1835--;

Column 23, line 13, "Hydroxproline" should read --Hydroxyproline--;

line 18, "Phenylaline" should read --Phenylalanine--;

line 33, "aminobenzoid" should read --aminobenzoic--;

line 44, "10-M" should read --$10^{-7}M$--.

Column 24, line 5, "1838" should read --1835--;

line 40, "cells" should read --cells,--;

Column 25, line 30, "hemotopoietic" should read --hematopoietic--.

Column 26, line 66, "may" should read --many--.

UNITED STATES PATENT AND TRADEMARK OFFICE
CERTIFICATE OF CORRECTION

PATENT NO.         : 6,667,034 B2
APPLICATION NO. : 08/857594
DATED                 : December 23, 2003
INVENTOR(S)       : Bernhard O. Palsson et al.

It is certified that error appears in the above-identified patent and that said Letters Patent is hereby corrected as shown below:

Column 27, line 9, "may removed form" should read --may be removed from--.

Column 28, line 42, "Methycellulose" should read --Methylcellulose--;

line 51, "means" should read --mean--.

Column 31, line 36, "$5 \times 10^8$" should read --$5 \times 10^6$--.

line 36, "$2 \times 10^8$" should read --$2 \times 10^6$--;

Column 31, line 59, "Hemotopoietic" should read --Hematopoietic--.

Column 32, line 36, "$1 \times 10^8$" should read --$1 \times 10^6$--;

line 41, "7" should read --17--.

Column 35, line 4, "of-cells" should read --of cells--.

Column 37, line 35, "Hematopoiesic" to --Hematopoiesis--.

Column 38, line 10, "LTBMCS" should read --LTBMCs--.

Column 40, line 54, "($V_3$)" should read --($V_2$)--; same line

"($V_3$) should read --($V_1$)--.

UNITED STATES PATENT AND TRADEMARK OFFICE
CERTIFICATE OF CORRECTION

PATENT NO. : 6,667,034 B2
APPLICATION NO. : 08/857594
DATED : December 23, 2003
INVENTOR(S) : Bernhard O. Palsson et al.

It is certified that error appears in the above-identified patent and that said Letters Patent is hereby corrected as shown below:

Column 41, line 51, "$(x10^4)$" should read --$(x10^{-6})$;

line 59, "IL-8" should read --IL-6--;

line 63, "$(V_3)$" should read --$(V_2)$--;

Column 43, line 16, "20000" should read --2000®--.

Column 44, line 33, "say" should read --day--.

Signed and Sealed this

Third Day of October, 2006

JON W. DUDAS
*Director of the United States Patent and Trademark Office*